United States Patent
Zapata Babio et al.

(10) Patent No.: US 7,402,382 B2
(45) Date of Patent: Jul. 22, 2008

(54) GEDAP METHOD (GENOTYPING BASED ON DIAGNOSTIC AMPLIFICATION PRODUCTS) FOR DETECTING AND/OR PREVENTING GENOTYPING ERRORS FROM AMPLIFICATION PRODUCTS OF A POLYMORPHIC FOCUS

(75) Inventors: Jose Carlos Zapata Babio, Santiago de Compostela (ES); Santiago Rodriguez Lopez, Santiago de Compostela (ES)

(73) Assignee: Universidade De Santiago De Compostela (ES)

( * ) Notice: Subject to any disclaimer, the term of this patent is extended or adjusted under 35 U.S.C. 154(b) by 200 days.

(21) Appl. No.: 10/481,943

(22) PCT Filed: Jun. 24, 2002

(86) PCT No.: PCT/ES02/00308

§ 371 (c)(1),
(2), (4) Date: Apr. 30, 2004

(87) PCT Pub. No.: WO03/001176

PCT Pub. Date: Jan. 3, 2003

(65) Prior Publication Data

US 2004/0219550 A1    Nov. 4, 2004

(30) Foreign Application Priority Data

Jun. 26, 2001    (ES) ................. 200101476

(51) Int. Cl.
*C12Q 1/68* (2006.01)
*C12P 19/34* (2006.01)

(52) U.S. Cl. ........................... 435/6; 435/91.2
(58) Field of Classification Search ............... None
See application file for complete search history.

(56) References Cited

U.S. PATENT DOCUMENTS

| | | | |
|---|---|---|---|
| 4,683,195 A | 7/1987 | Mullis et al. | 435/6 |
| 5,874,212 A | 2/1999 | Prockop et al. | 435/6 |
| 5,876,933 A | 3/1999 | Perlin | 435/6 |
| 2002/0042061 A1 * | 4/2002 | Yang et al. | 435/6 |

FOREIGN PATENT DOCUMENTS

| | | |
|---|---|---|
| WO | WO 90/13668 | 11/1990 |
| WO | WO 9013668 A1 * | 11/1990 |
| WO | WO 95/01453 | 1/1995 |
| WO | WO 9501453 A1 * | 1/1995 |
| WO | WO 99/35284 | 7/1999 |

OTHER PUBLICATIONS

Wilkin et al. Heteroduplex analysis can increase the informativeness of PCR-amplified VNTR markers: application using a marker tightly linked to the COL2A1 gene. Genomics. Feb. 1993;15(2):372-5.*

Espejo et al. ("Detection of HIV1 DNA by a simple procedure of polymerase chain reaction, using "primer-dimer" formation as an internal control of amplification" Res Virol. May-Jun. 1993;144(3):243-6).*

Higashimoto et al. "Rapid detection of FGFR mutations in syndromic craniosynostosis by temporal temperature gradient gel electrophoresis" Clinical Chemistry (1999), 45(11), 2005-2006.

Narita, T. et al. "Heteroduplex analysis: a useful screening method for glycogen storage disease type Ia." Diagnostic molecular pathology, (Apr. 1998) 7 (2) 111-3.

Martinelli, G. et al. "Detection of clonality by heteroduplex analysis of amplified junctional region of T-cell receptor γ in patients with T-cell acute lymphoblastic leukemias" Haematologica (1997), 82(2), 161-165.

Savage, D. et al. "Detection of β thalassemia mutations using DNA heteroduplex generator molecules" British Journal of Haematology (1995), 90(3), 564-71.

* cited by examiner

*Primary Examiner*—Kenneth R. Horlick
*Assistant Examiner*—Christopher M. Babic
(74) *Attorney, Agent, or Firm*—Ostrolenk, Faber, Gerb & Soffen, LLP

(57) ABSTRACT

Method GEDAP (Genotyping Based on Diagnostic Amplification Products) for detecting and/or preventing genotyping errors on the basis of the amplification products of a polymorphic locus. The method is based on the joint analysis of homoduplexes and Diagnostic Additional Products (DAPs) generated from the amplification of a polymorphic locus. The method is highly effective for detecting and/or preventing genotyping errors due to total or partial non-amplifications occurring during amplification procedures such as the Polymerase Chain Reaction (PCR).

20 Claims, 12 Drawing Sheets

GEDAP METHOD (GENOTYPING BASED ON DIAGNOSTIC AMPLIFICATION PRODUCTS) FOR DETECTING AND/OR PREVENTING GENOTYPING ERRORS FROM AMPLIFICATION PRODUCTS OF A POLYMORPHIC FOCUS

Method GEDAP (Genotyping Based on Diagnostic Amplification Products) for detecting and/or preventing genotyping errors on the basis of the amplification products of a polymorphic locus.

CROSS-REFERENCE TO RELATED APPLICATIONS

This application is a 35 U.S.C. 371 U.S. National Stage conversion of International Application No. PCT/ES02/00308 filed Jun. 24, 2002 which, in turn, claims the priority of Spanish application No. P0101476 filed Jun. 26, 2001, the contents of which are specifically incorporated herein by reference thereto. The International application was published in the Spanish language.

TECHNICAL FIELD

A method for genotyping polymorphic loci by analysing the products generated from the amplification of alleles contained in diploid or polyploid samples. More specifically, it is a method for detecting and/or preventing genotyping errors due to total or partial non-amplifications of alleles, produced during the amplification procedure. It also pertains to genetic applications and systems which can effectively use genotyping information of this type, such as disease diagnosis, pre-implantational genetic diagnosis, paternity testing, forensic analyses, genetic therapy, tissue and organ transplantation, pharmacogenetics, population genetics, genome mapping and genetic epidemiology.

BACKGROUND OF THE INVENTION

Genotyping is the mandatory starting point for most genetic analyses, both basic and applied, and has contributed decisively to the development of genetics and its applications. The genotyping of polymorphic DNA loci has recently been facilitated by two fundamental advances: the invention of the Polymerase Chain Reaction (PCR) (Saiki et al., 1985; Mullis et al., 1986) and the discovery of a fairly even spread of polymorphic DNA sequences throughout genomes (mainly DNA markers composed of tandem arrays of motifs one or more base pairs long) (Dib et al., 1996; Tóth et al., 2000). Both advances have contributed decisively towards understanding of the structure and function of genomes of living organisms, and towards the development of population genetics, genetic epidemiology, genome mapping, genetic therapy, disease diagnosis, preimplantational genetic diagnosis, forensic analysis, tissue and organ transplantation, pharmacogenetics, paternity testing, etc.

The conventional methods used for genotyping polymorphic DNA loci are based on the following strategy: (a) amplifying the locus alleles present in a sample (generally by means of PCR); (b) identifying the amplified alleles (generally by means of electrophoresis); and (c) determining the sample genotype from the amplified alleles.

This genotyping strategy should guarantee that the genotype determined from amplification products is in fact the actual sample genotype. In practice, however, conventional genotyping methods carry associated a percentage of error, which is dependent on the experimental conditions used.

Genotyping errors have very negative consequences in genetic analyses and in the applications derived from such analyses. Obviously, genotyping errors may have serious consequences if they lead to the erroneous identification of human individuals (e.g. in criminal analyses, in paternity testing, etc.). Likewise, genotyping errors may lead to wrong medical diagnoses which may be especially pernicious in disease diagnosis, preimplantational diagnosis, tissue and organ transplantation, etc. On the other hand, it is known that genotyping errors negatively influence the accuracy of genetic analyses, leading to serious drawbacks such as loss of power in gene-mapping studies, significant distortion of map distances and false exclusion of the true location of a disease-predisposing gene (Buetow, 1991; Goldstein et al., 1997; Göring and Terwilliger, 2000). The negative effects of genotyping errors may be even greater in gametic disequilibrium analyses (Zapata et al., 2001a; Zapata et al., 2001b), because a single genotyping error can destroy evidence of past non-recombinant meioses (Terwilliger et al., 1997; de La Chapelle and Wright, 1998; Göring et al., 1997; Göring and Terwilliger, 2000; Akey et al., 2001).

An important source of genotyping errors is the occurrence of problems during amplification that lead to the total or partial absence of the amplification product of, at least, one of the alleles originally present in the sample. The partial absence of the amplification product of an allele, or partial non-amplification, is also known as preferential amplification (Walsh et al., 1992). The total absence of the amplification product of an allele, or total non-amplification, is known as allele dropout (Findlay et al., 1995; Gagneux et al., 1997) or null allele (Pemberton et al., 1995).

The occurrence of this type of problem during the amplification procedure has serious consequences. In the case of heterozygous diploid samples, total non-amplifications and some partial non-amplifications lead to the incorrect genotyping of the sample as homozygous (Demers et al., 1995; Findlay et al., 1995; Pemberton et al., 1995; Fishback et al., 1999; Anderson et al., 2000).

In view of the serious consequences of genotyping errors in genetic analyses and in genetic applications, considerable efforts have been made:

1.—to identify the causes of total and partial non-amplifications;

2.—to detect and/or prevent genotyping errors due to total and partial non-amplifications.

1.Causes of total and partial non-Amplifications

Recent analyses have revealed the common causes of total and partial non-amplification. The partial non-amplification of one allele in diploid samples can result from several factors such as: (a) significant GC% differences between alleles from a heterozygous sample (these differences can allow the denaturation of one allele but not the other, phenomenon known as differential denaturation) (Walsh et al., 1992); (b) between-allele length differences, resulting in the preferential amplification of the shorter allelic product (probably favoured when Taq polymerase is limiting) (Walsh et al., 1992); (c) stochastic fluctuations in the number of copies of each allele (Walsh et al., 1992); (d) mismatches between the primers and one allele (which may result from mutations in the priming region) (Walsh et al., 1992); (e) damage to the DNA template (by ultraviolet irradiation or by monovalent salts such as sodium chloride, sodium acetate or ammonium acetate) (Mutter and Boynton, 1995); (f) low-stringency primer annealing (which may result from the coamplification either of the locus and an internal control for sizing the amplified alleles, or of more than one polymorphic sequence) (Weissensteiner and Lanchbury, 1996).

It has been suggested that total non-amplification may result from extreme partial non-amplification (Findlay et al., 1995; Ronai et al., 2000). Therefore, mechanisms that lead to partial non-amplification can also lead to total non-amplification. In addition, other evidence shows that the total non-amplification rate is especially high when template concentration in the sample is low (Gagneux et al., 1997; Lissens and Sermon, 1997). This is the case when the genotyping is done either from a single cell (for instance, in preimplantational genetic diagnosis), or from biological remains that are degraded and/or retain little DNA (as may occur in several forensic analyses). In these cases, total non-amplification is favoured by factors such as (a) chromosomal mosaicism, and more specifically the presence of haploid cells in an otherwise diploid embryo (Harper et al., 1995); (b) the method used for lysing the cell before PCR (Lissens and Sermon, 1997, and references therein); (c) the denaturation temperature at the start of the first PCR cycle (Ray and Handyside, 1996); (d) DNA breaks produced by endogenous endonucleases (Lissens and Sermon, 1997); (e) suboptimal PCR conditions (Handyside and Delhanty, 1997); and (f) rapid degradation of the target DNA during thermocycling (Handyside and Delhanty, 1997).

2. Detection and/or Prevention of Genotyping Errors Due to Total or Partial Non-Amplifications Several improvements of conventional genotyping methods have been proposed for detecting and/or preventing genotyping errors due to total and partial non-amplifications. Basically, these may be divided into two categories: (2.1) direct methods and (2.2) indirect methods.

2.1. Direct Methods

Direct methods are based on (a) improvement of amplification conditions for preventing the occurrence of total or partial non-amplifications and (b) improvement of the system for the detection of amplified alleles.

(a) Improvement of amplification conditions

Several optimizations of amplification conditions have been suggested for trying to prevent the occurrence of partial non-amplifications, including: (a) not using either a DNA template concentration higher than 200 ng or an extension time longer than 2 min (Deka et al., 1992); (b) substitution of dGTP either for 7-deaza-2'-dGTP (Mutter and Boynton, 1995) or for 2'-desoxyinosine-5'-triphosphate (dITP) (Ronai et al., 2000); (c) using PNA (Peptide Nucleic Acid) during the amplification procedure (Demers et al., 1995); (d) using double-strand-destabilizing cosolutes such as betaine and glycerol (Weissensteiner and Lanchbury, 1996); (e) increasing the KCl concentration (Fishback et al., 1999).

Optimizations of amplification conditions that have been suggested for reducing the occurrence of partial non-amplifications include: (a) increasing the denaturation temperature (Lissens and Sermon, 1997); (b) carrying out whole-genome amplification by primer extension pre-amplification (PEP) followed by nested PCR (Handyside and Delhanty, 1997); (c) approaches for increasing the DNA-template amount, such as biopsy of more than one embryo cell (Harper et al., 1996), or increase in the number of fetal cells isolated from maternal fluids (Garvin et al., 1998), etc.

(b) Improvement of the System for the Detection of Amplified Alleles

Similarly, improvements in the system for the detection of amplified alleles have been suggested for the detection of genotyping errors due to total and partial non-amplifications. For instance, Findlay et al. (1995) have demonstrated that fluorescent PCR decreases the genotyping error rate due to total and partial non-amplifications. This is because fluorescent PCR, which is much more sensitive than conventional PCR, allows detection of samples which are classified by conventional PCR as homozygotes but which are in fact heterozygous with extreme partial non-amplification.

In this connection, it has been pointed out that the definitive method for high-resolution genotyping is the detection of polymorphisms through fluorescent-automatic-sequencing by the use of automated sequencers based on capillary electrophoresis, such as the ABI PRISM 310 or the ABI PRISM 3100 (Applied Biosystems, 2001). This approach could potentially detect genotyping errors due to partial non-amplifications. Nevertheless, the genotyping problem associated with total non-amplification remains unresolved when automated sequencers such as the ABI PRISM 310 are used (Garvin et al., 1998). In fact, several authors have recently indicated that genotyping errors are inevitable (Douglas et al., 2000; Göring and Terwilliger, 2000) and more difficult or impossible to detect when Mendelian information is unavailable (Weeks et al., 2000).

Consequently, the suggested improvements of amplification conditions or of the detection system do not eliminate all partial or total non-amplifications, and do not ensure detection of all genotyping errors due to these PCR errors.

2.2. Indirect methods

An alternative for detecting genotyping errors due to total or partial non-amplification is to resort to indirect methods such as: (a) replicating the amplification a sufficient number of times to obtain a reliable genotype, and (b) Mendelian analysis.

(a) Amplification replicates

It has been suggested that three replicates of one sample (i.e., repeating the amplification and detection of amplified alleles three times) should detect 95% of genotyping errors due to total or partial non-amplifications (Gagneux et al., 1997). Taberlet et al. (1996) have suggested that this percentage may be increased to 99% when seven replicates are performed, although this remains controversial (Weissensteiner, 1997; Taberlet, 1997).

Nevertheless, this strategy has two main limitations. First, it does not allow a priori identification of the samples with total or partial non-amplification. Therefore, it is necessary to carry out several PCR replicates of all apparent homozygotes, given that conventional genotyping methods do not distinguish between homozygous samples and heterozygous samples with total non-amplification. Obviously, this approach is hardly applicable in studies in which a large number of individuals are analyzed (e.g. in genome scans and in many population and epidemiological analyses). Second, the applicability of this strategy is seriously limited by DNA availability, because the amount of DNA is often very reduced (for instance, in preimplantational genetic analyses, in forensic studies in which samples are degraded or contain very little DNA, as in the case of hairs, etc.).

(b) Mendelian analysis

Another indirect method valuable for detecting a broad range of genotyping errors is Mendelian analysis (Ewen et al., 2000). However, this procedure is not always applicable, because samples biologically related with the sample of interest are not always available. Moreover, genotyping errors may not always be readily detectable as inconsistencies in Mendelian inheritance, especially in studies of small families (Weeks et al., 2000).

In view of the above, it is evident that conventional methods, based on genotyping from amplified alleles, are not effective for detecting and/or preventing genotyping errors due to total or partial non-amplification. Notably, such errors occur even after the use of direct and indirect methods for detecting and/or preventing them specifically. There is thus a clear need for new genotyping methods that are effective for detecting and/or preventing genotyping errors due to total or partial non-amplifications.

Recent evidence suggests that several products generated by PCR during allele amplification (particularly heteroduplexes) may be used as an additional source of information in the identification of heterozygous samples (Wilkin et al., 1993; Neilan et al., 1994; Ardren et al., 1999) and in the detection of homoplasy (Szibor et al., 1996; Haddad et al., 1997; Ardren et al., 1999). As far as we know, however, these reports have not considered the possibility that additional products other than the amplified alleles themselves may be of value in the detection and/or prevention of genotyping errors originating from total or partial non-amplifications.

SUMMARY OF THE INVENTION

The present invention is a genotyping method, called Genotyping Based on Diagnostic Amplification Products (GEDAP), which enables the detection and/or prevention of genotyping errors due to total or partial non-amplification. The method is reproducible, reliable and accurate. It is based on a genotyping strategy different to that used in conventional methods. The GEDAP method consists of inducing the formation of homoduplexes of amplified alleles and other Diagnostic Additional Products (DAPs), and analyzing them jointly to determine the genotype of a locus from a diploid or polyploid sample. Most notably, it promotes the formation of genotype-specific DAPs and allele-specific DAPs. The joint analysis of these two types of DAP together with the homoduplexes of the amplified alleles is used in the GEDAP method to reveal whether a total or a partial non-amplification of at least one allele has been produced, or not, during the amplification of the polymorphis locus of interest.

Thus, in one aspect, GEDAP allows the detection of genotyping errors due to total or partial non-amplifications, on the basis of the detection of anomalous combinations of homoduplexes and DAP. In other aspect, it also allows the prevention of genotyping errors due to total or partial non-amplifications, on the basis of the detection of expected combinations of homoduplexes and DAP genotype-specifics.

The GEDAP method to a great extent resolves the limitations of conventional methods. Thus, it allows the precise identification of amplification products associated with total or partial non-amplifications, considerably reducing the number of PCR replicates needed to detect genotyping errors associated with these problems. On the other hand, the GEDAP method provides an internal control of PCR quality, so that it is unnecessary to resort to indirect methods for detecting and/or preventing genotyping errors. In addition, it may be partially or totally automated, for what it may be used to optimize high throughput genotyping.

The GEDAP method is applicable to all diploid or polyploid organisms, including animals and plants. It is equally applicable for genotyping transgenic and cloned organisms. In practice, the method is likely to be used mainly in medical contexts and for commercially profitable applications.

By way of illustration, we demonstrate that the GEDAP method allows the effective detection and/or prevention of genotyping errors due to total or partial non-amplifications produced during the amplification of dinucleotide-repeat microsatellites. It is therefore useful for applications derived of the use of these DNA markers. In the biotechnological industry it may be applied, for instance, in disease diagnosis, preimplantational genetic diagnosis, genetic therapy, tissue and organ transplantation, pharmacogenetics, paternity testing, forensic analyses, and in the elaboration or improvement of genotyping software. In basic science, it may be applied, for instance, in population genetics and in genome mapping.

These and other objects, features and advantages of the new genotyping method will be clear to a person of ordinary skill in the art upon reading the following detailed description in light of the append drawings.

DETAILED DESCRIPTION OF CERTAIN PREFERRED EMBODIMENTS

Figure 1:
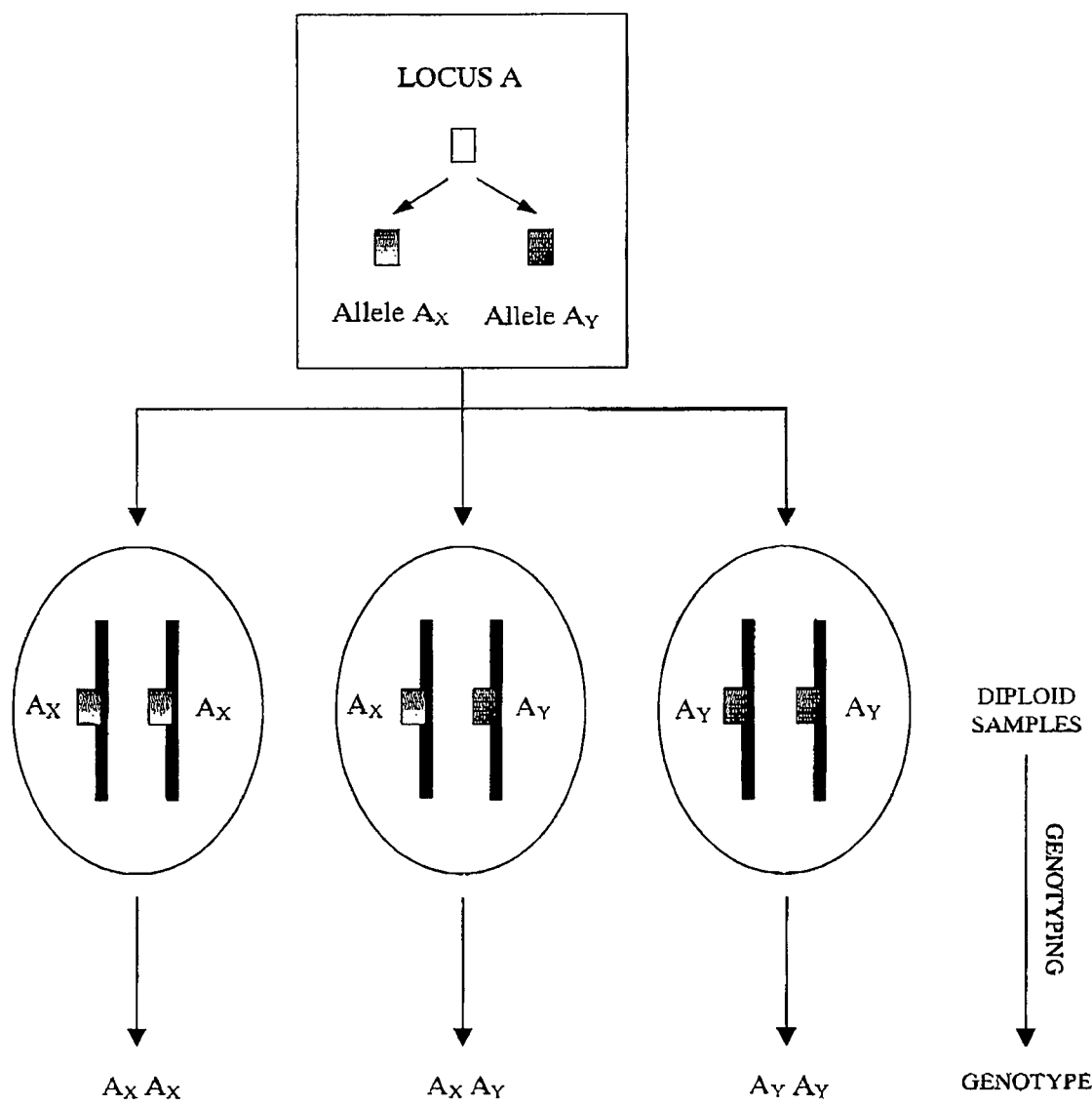
FIG. 1 provides a schematic illustration of the genotyping of a polymorphic locus (A) having two different alleles ($A_X$, $A_Y$) from diploid samples.

In this section, we describe in detail how to apply the GEDAP method. Firstly, we describe how to generate and identify the homoduplexes and the Diagnostic Additional Products (DAPs). Secondly, we describe how genotyping errors may be detected and/or prevented, and the advantages of GEDAP with regard to conventional methods. Thirdly, we evaluate the efficacy of the method. Finally, we show two examples for elucidating some of the applications of the present invention.

A) Generation and Identification of Homoduplexes and DAP

The GEDAP method can genotype any locus comprising a nucleic acid sequence with at least two different alleles. In the preferred embodiment, the locus is any DNA marker with tandem repetitions of one or more nucleotides.

The genotyping begins with the obtention of any sample containing, or suspected of containing, at least two alleles from the locus of interest. In the preferred embodiment, the samples are blood samples from human individuals.

The locus alleles are then amplified under homoduplex- and DAP-inducing conditions. The amplification can be carried out from the nucleic acids contained in the sample, without isolating them from the remaining sample components (e.g. Yue et al., 2001). Another possibility is to purify the nucleic acids prior to amplification. In the preferred embodiment, the DNA is isolated prior to allele amplification. There are numerous standard methods to isolate DNA from whole blood, other tissues, hair, faeces, saliva, etc. In the preferred embodiment, the DNA is isolated using a commercial kit for extracting DNA from whole blood samples (QIAamp blood kit, QIAGEN).

A suitable technique for amplifying the locus alleles under conditions favouring homoduplexes and DAP formation, is the Polymerase Chain Reaction (PCR), although other DNA or RNA amplification procedures such as Nucleic Acid Sequence Based Amplification (NASBA), the Transcription-based Amplification System (TAS), Self-sustained Sequence Replication (3SR), Q-beta replicase, Ligation Amplification Reaction (LAR) and the Ligase Chain Reaction (LCR) (Dr bek, 2001) can be used. PCR allows the in vitro amplification of one or more specific sequences of DNA present in a nucleic acid, or mixture of nucleic acids, using primers and agents for polymerization. The extension product of one primer, when hybridized to the other, becomes a template for the production of the desired specific nucleic acid sequence, and viceversa. This process is repeated as often as is necessary to produce the desired amount of the sequence. The following method for PCR amplification is standard, and can be readily applied to amplify every microsatellite DNA marker with tandem repetitions of one or more nucleotides.

In the preferred embodiment to carry out the PCR amplification, the nucleic acid of the sample is mixed with the other components of the PCR reaction. These other components include, but are not limited to, the standard PCR buffer (containing Tris pH 8.0, 50 mM KCl, 2.5 mM magnesium chloride), the triphosphate deoxynucleotides (dTTP, dCTP, dATP, dGTP), and the thermostable polymerase (e.g. Taq polymerase). The total amount of each mixture component is determined by the final volume of each PCR reaction and the number of reactions.

The primer sequences and the specific conditions suitable for amplifying each marker can be obtained from available databases. The primers for amplifying each marker can be synthesized (see, for instance, Beacauge et al. 1981; Caruthers et al. 1988; Haralambidis et al. 1990) or purchased from commercial vendors. Primers may also be derivatized to facilitate their detection (for instance: with fluorochromes, radioisotopes, ligands for chemiluminescent detection, ligands such as digoxigenin for immunochemical detection, etc.).

The PCR reactions are performed by heating and cooling the reaction mixture to specific locus-dependent temperatures that are given by the known PCR conditions. Typically, the thermocycling protocol consists of:
  a) An initial denaturation step (e.g. 94° C. for 3 minutes)
  b) Repeat from 20 to 40 times:
    b1.—a denaturation step (e.g. 94° C. for 30 seconds)
    b2.—an annealing step (e.g. 55° C. for 30 seconds)
    b3.—an elongation step (e.g. 72° C. for 30 seconds)
  c) A final elongation step (e.g. 72° C. for 2 minutes).

The experimental conditions used in PCR favour the generation of homoduplexes of the amplified alleles and the generation of other additional products, including DAP. The denaturation of nucleic acids present in the reaction mixture used during the PCR, and their subsequent renaturation, is a particularly important source of homoduplexes and other additional products. The number of homoduplexes and additional products generated in PCR depends, firstly, on whether the nucleic acids resulting from the amplification have a different sequence or not. Thus, in reaction mixtures of homozygous samples (in which locus alleles have the same sequence), the consecutive cycles of denaturation and renaturation will generate a single type of homoduplex. On the contrary, in reaction mixtures of heterozygous samples (in which at least two locus alleles have a different sequence), such cycles will generate a number of homoduplexes equal to the number of different sequences present in these reaction mixtures. In addition, in heterozygous samples, the subsequent denaturation-renaturation cycles also will induce heteroduplexes resulting from the hybridization of two strands of nucleic acids with different sequences.

In addition to the aforementioned homoduplexes and heteroduplexes, PCR also induces the formation of other types of additional products. For instance, when Taq polymerase carries out the elongation procedure, it may make mistakes that lead to the synthesis of nucleic acids with a sequence different to the sequence of the DNA template. One such mistake produced by the mechanism known as DNA slippage, occurs with relative frequency in the amplification of microsatellite markers with tandem repetitions of one or more nucleotides. Thus, in the case of dinucleotide-repeat microsatellite markers, the slippage gives rise to the formation of nucleic acids with a gain or a loss of one repeat unit (2 nucleotides) in relation to the original DNA template (although the probability of losing a repeat unit is much greater than that of gaining one; Miller and Yuan, 1997). The subsequent denaturation-renaturation cycles will thus induce double-stranded nucleic acids, different to the homoduplexes, resulting from the hybridization of two complementary strands generated by slippage. In the same way, new heteroduplexes resulting from the hybridization between the strands generated by slippage and the allele strands can also be formed.

It has been reported that some oligonucleotides can bind to double-stranded DNA, forming stable intermolecular triplexes (Durland et al., 1991; for review see Frank-Kamenetskii and Mirkin, 1995). Another possible source of additional products in PCR is therefore the generation of triplexes through the binding of at least one of the primers used in the amplification and one or more of the double-stranded nucleic acids present in the reaction mixture. Other components of the reaction mixture used in the amplification may also induce the formation of intermolecular triplexes. Thus, it has been reported that the DNA analog Peptide Nucleic Acid (PNA), used in PCR for enhancing DNA amplification and reducing the occurrence of preferential amplification (Demers et al., 1995), also induces triplex formation (for review see Frank-Kamenetskii and Mirkin, 1995).

Once the PCR has finished, additional products may still be generated. Among the potential causes of the generation of such additional products are the formation of complexes among the reaction mixture components, and the occurrence of conformational changes in the nucleic acids generated by PCR. For instance, it is known that DNA fragments with tandem repetitions of the CA dinucleotide associate spontaneously with each other in vitro, forming stable four-stranded structures that can be detected by gel electrophoresis and electron microscopy (Gaillard and Strauss, 1994). In the same way, the GA motif confers remarkable conformational polymorphism on DNA, with possible conformations including tetraplexes (Lee, 1990), single-stranded acid fold (Dolinnaya and Fresco, 1992; Dolinnaya et al., 1993; Ortiz-Lombardía et al., 1995), parallel-stranded duplex (Lee, 1990), antiparallel-stranded duplex (Huertas et al., 1993; Casasnovas et al., 1993), zinc-specific duplex (Ortiz-Lombardía et al., 1995) and tetraplex composed of two hairpins (Shiber et al., 1996; Mukerji et al., 1996). Other motifs, such as the AT motif, likewise confer conformational polymorphism on DNA (see Vorlícková et al., 1998 and references therein).

The formation of such additional products once the PCR has finished may be spontaneous. The generation of these additional products can also be deliberately induced by specific experimental conditions. One approach is to first denature the amplification products by use of some physical, chemical or biological procedure (such as thermal denaturation, electrochemical denaturation by application of voltage, the use of denaturing agents like formamide, urea or EDTA, or enzymes), then to renature the products again. Other approaches for inducing the formation of additional products include subjecting the amplification products to changes in temperature, salt concentration, pH or the concentration of bivalent ions (see, for instance, Dolinnaya and Fresco, 1992; Noonberg et al., 1995; Ortiz-Lombardía et al., 1995; Vorlícková et al., 1998; for review see Frank-Kamenetskii and Mirkin, 1995).

Once the homoduplexes and the additional products have been generated, the analyst can proceed to identify the amplification products needed for genotyping the sample, i.e., the homoduplexes and the DAPs. For identifying them, one can use any-nucleic acid identification system which maintains at least some of the homoduplexes and DAPs generated previously. For optimal application of the claimed method, however, it is more useful to use a system which not only maintains the existing homoduplexes and DAPs but also offers the capability to generate new DAPs.

DNA electrophoresis under non-denaturing conditions is a suitable system both for maintaining homoduplexes and DAPs, and for generating new DAPs. It is well known that non-denaturing electrophoresis is a very sensitive means of separating and identifying of a wide variety of DNA conformations. Thus, it is known that triplexes remain intact during electrophoresis in magnesium-containing polyacrylamide gels (Durland et al., 1991). Similarly, non-denaturing electrophoresis is one of the systems used for detecting the presence of tetraplexes (Lee, 1990), single-stranded acid fold (Dolinnaya and Fresco, 1992; Dolinnaya et al., 1993; Ortiz-Lombardía et al., 1995), parallel-stranded duplexes (Lee, 1990), antiparallel-stranded duplexes (Huertas et al., 1993; Casasnovas et al., 1993), zinc-specific duplexes (Ortiz-Lombardía et al., 1995), tetraplexes composed of two hairpins (Shiber et al., 1996; Mukerji et al., 1996), etc. Therefore, non-denaturing electrophoresis allows maintenance not only of homoduplexes but also of additional products generated during or after amplification.

It is also known that non-denaturing electrophoresis can promote the formation of additional products, such as intermolecular triplexes. For instance, non-denaturing electrophoresis generates triplexes when a faster migrating single strand overtakes a slower migrating band containing a duplex of appropriate sequence ("capture in the gel"; Belotserkovskii and Johnston, 1996). In addition, the formation of double-hairpin tetraplex has been reported to occur when a high ionic strength is used during non-denaturing electrophoresis (Shiber et al., 1996). Similarly, it is known that non-denaturing electrophoresis generates bands different to allele bands in analyses of some microsatellite markers. These new bands probably originate from alterations of the double helix curvature (Lareu et al., 1998) or by hairpin loop formation in AT-rich sequences (Prinz et al., 1996).

Besides maintaining existing homoduplexes and DAPs, and generating new DAPs, DNA electrophoresis under non-denaturing conditions allows the identification of homoduplexes and DAPs on the basis of their physical separation through the effects of the electrical field. Once the electrophoresis has finished, one can proceed to observe the generated bands by any means that allows the detection of DNA, such as silver staining, ethidium bromide staining, etc.

It should be stressed that non-denaturing electrophoresis is the preferred technique of identification, but that the present claim extends to any appropriate technique. Specifically, any technique allowing the identification of homoduplexes and DAPs can be used, such as mass spectrometry, chromatography, differential hybridization, sequencing by hybridization, etc.

Once the homoduplexes and the DAPs have been identified, one can proceed to infer the sample genotype by the GEDAP method.

B) Basis and Advantages of the GEDAP Method

The basis and the advantages of the proposed method will become apparent in the following comparison of conventional genotyping methods and the GEDAP method. This comparison is established taking as an example the genotyping of a polymorphic locus with two alleles from diploid samples (FIG. 1).

Figure 2:
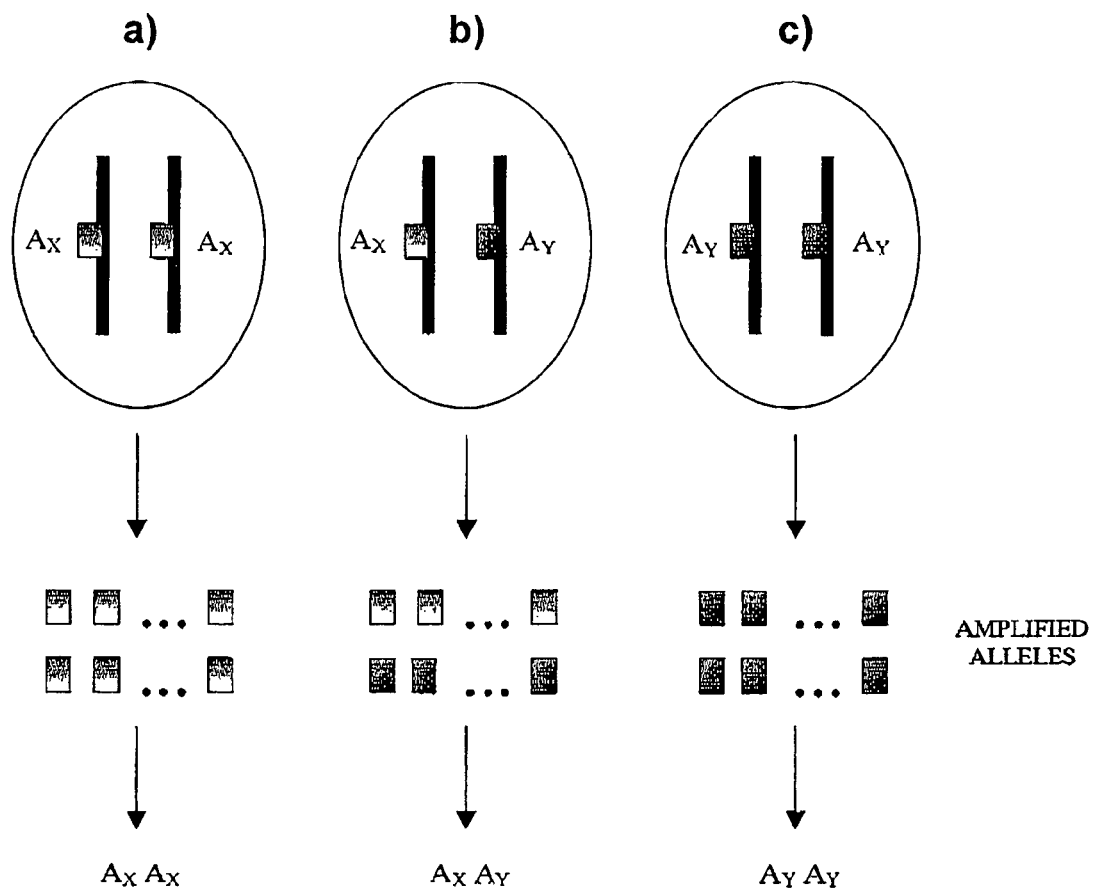
FIG. 2 provides a schematic illustration of the basis of conventional genotyping methods.

The outstanding difference between the GEDAP method and conventional genotyping methods is in the additional products generated during or after the amplification. Thus, conventional methods are based on the genotyping of a polymorphic locus taking into account only the alleles amplified from the sample (FIG. 2). Any other additional product is considered artefactual, and as such something that should ideally be minimized or eliminated (see for instance Perlin et al. 1994, Schlötterer, 1998). Therefore, under optimal conditions, homozygous samples will give only one amplified allele (FIG. 2, $a$ and $c$), while heterozygous samples will give two different amplified alleles (FIG. 2, $b$).

Figure 3:
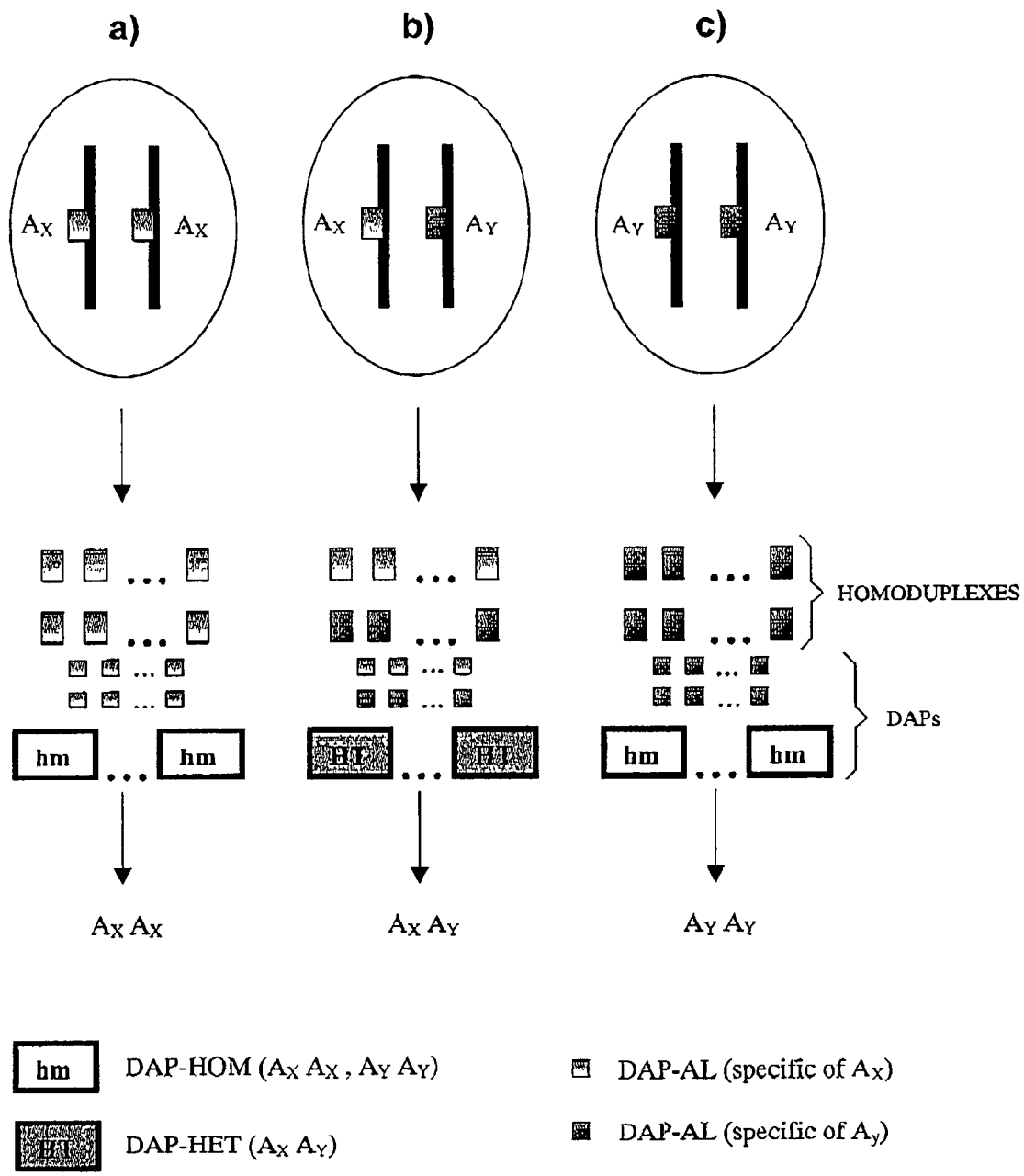
FIG. 3 provides a schematic illustration of the basis of the GEDAP method.

On the contrary, the GEDAP method is based on the genotyping of a polymorphic locus from the joint analysis of the identified homoduplexes and DAPs (FIG. 3). The DAPs are considered to provide additional information useful for corroborating the sample genotype, and these components are thus deliberately induced. The DAPs useful for genotyping can be divided into two different types: additional genotype-diagnostic products (DAP-HOM and DAP-HET) and additional allele-diagnostic products (DAP-AL). The presence of such DAP types emphasizes the differences existing between homozygous and heterozygous samples. Thus, under optimal conditions, homozygous samples will give only one homoduplex, with at least one DAP-HOM and at least one DAP-AL specific for that homoduplex (FIG. 3, $a$ and $c$). On the contrary, heterozygous samples will give two homoduplexes, with at least one DAP-HET and at least one DAP-AL specific for each homoduplex (FIG. 3, $b$).

Figure 4:
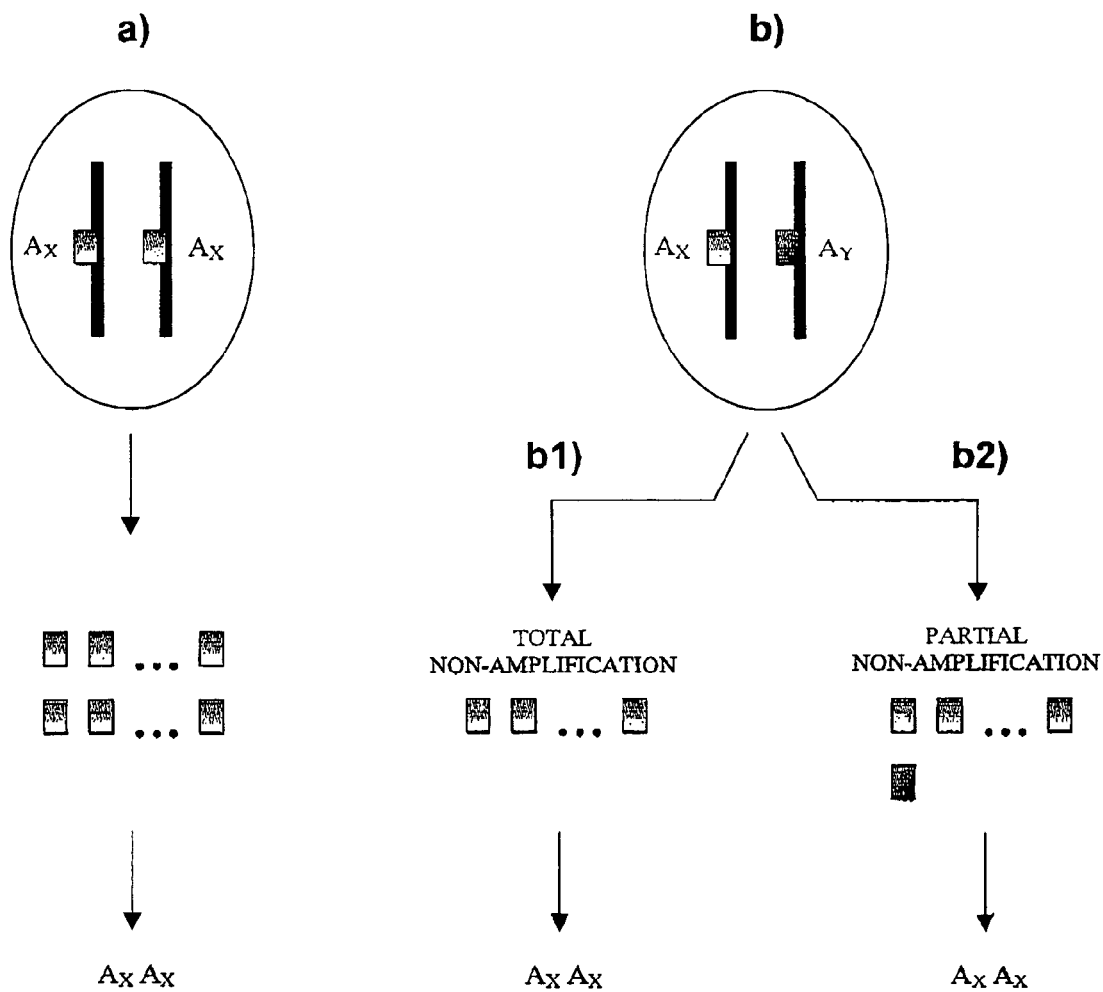
FIG. 4 provides a schematic illustration of those types of genotyping error due to total or partial non-amplification which are neither detected nor prevented by conventional genotyping methods.

The different approaches used in conventional genotyping methods and in the GEDAP method result in a different capability for detecting and/or preventing genotyping errors due to total and partial non-amplifications. Thus, conventional methods do not allow distinction between heterozygous samples with total non-amplification (FIG. 4, $b1$) and genuinely homozygous samples (FIG. 4, $a$), because both give only one amplified allele. On the other hand, heterozygous samples with partial non-amplification (FIG. 4, $b2$) may be mistaken for homozygous samples (FIG. 4, $a$), especially if the amount of hypoamplified allele is below the threshold detection level. Conventional methods are therefore ineffective in both circumstances, both for detecting and for preventing genotyping errors.

Figure 5:
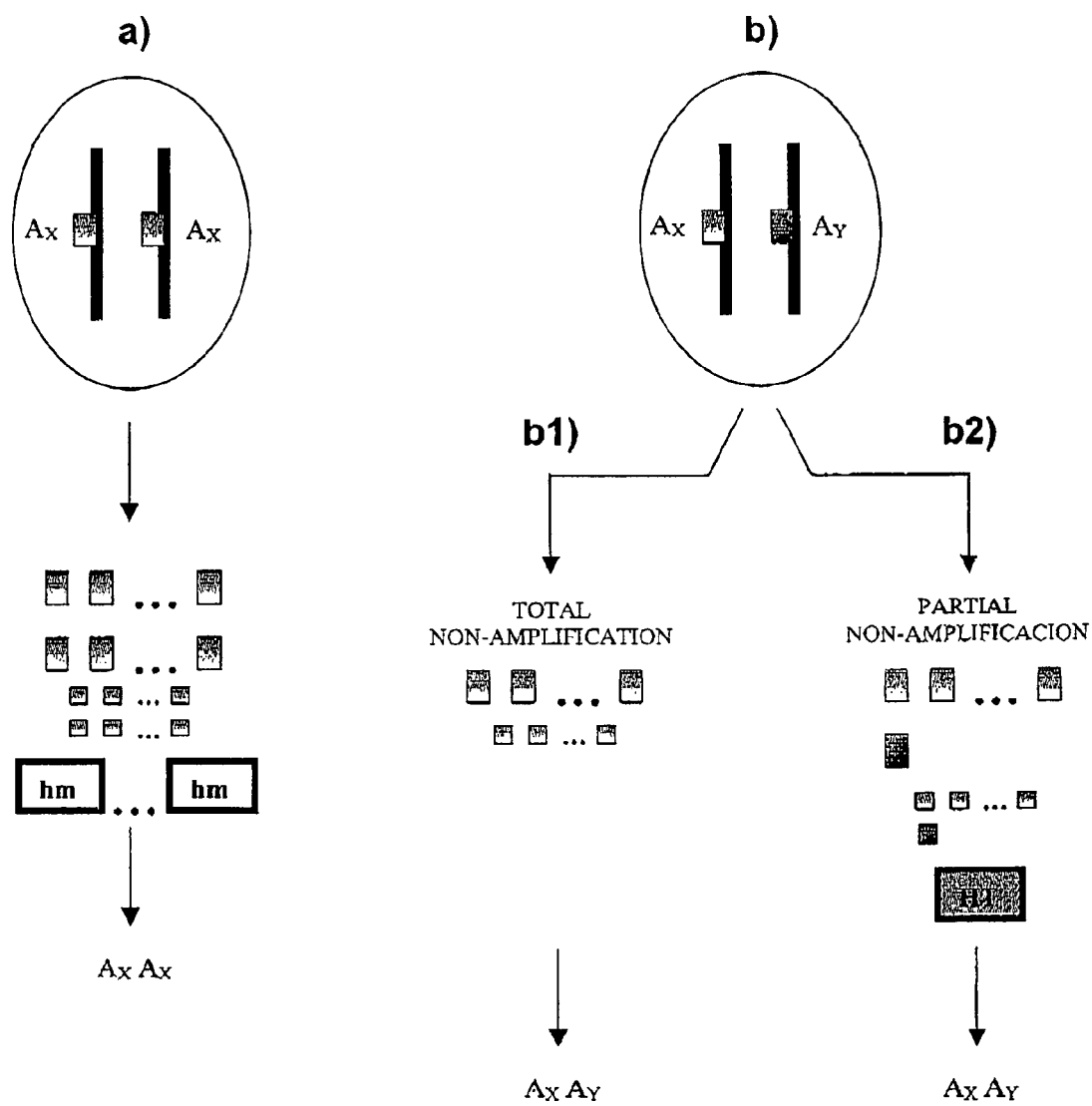
FIG. 5 provides a schematic illustration of the detection and prevention by the GEDAP method of genotyping errors due to total and partial non-amplifications.

By contrast, the GEDAP method enables effective detection and/or prevention of genotyping errors in both cases. On the one hand, the GEDAP method enables discrimination between heterozygous samples with total non-amplification and genuinely homozygous samples. This is due to the fact that, although both types of samples give a single homoduplex, there are differences between them as regards the DAPs. Thus, heterozygous samples with total non-amplification do not give DAP-HOMs (FIG. 5, b1), while genuinely homozygous samples do give DAPs of this type (FIG. 5, a). On the other hand, the GEDAP method also eliminates the confusion between heterozygous samples with partial non-amplification and genuinely homozygous samples. This is due to the fact that heterozygous samples with partial non-amplification may be identified by the presence of DAP-ALs specific for the two homoduplexes and/or by the presence of DAP-HETs (FIG. 5, b2), both types of DAPs being absent in genuinely homozygous samples (FIG. 5, a).

In short, the GEDAP method allows the detection of genotyping errors by the identification of anomalous combinations of homoduplexes and DAP; it also ensures the prevention of genotyping errors by the identification of expected combinations of genotype-specific homoduplexes and DAPs. In both cases, the consideration of DAP-HOMs, DAP-HETs and DAP-ALs is a fundamental level of control for determining whether a sample genotype is homozygous or heterozygous.

C) Efficacy of the GEDAP Method

The efficacy of the GEDAP method can be estimated statistically. Specifically, one can test whether the genotype frequencies observed in a population sample deviate significantly from the genotype proportions expected under Hardy-Weinberg (HWP). Analyses that concentrate departures from HWP in a single degree of freedom (Gomes et al., 1999), together with large sample sizes, greatly increase power in the detection of such departures. This type of statistical analysis is a very powerful means for detecting genotyping errors (Chakraborty et al., 1992; Gomes et al., 1999). Most importantly, non-amplifications of one of the alleles present in heterozygous samples lead to a heterozygote deficiency relative to HWP. Therefore, if one genotypes a large populational sample and detects no significant departure from HWP, one can conclude that the GEDAP method is effective for detecting and/or preventing genotyping errors.

D) Applications of the GEDAP Method

In this section, we list some of the applications of the GEDAP method, in two representative contexts: the genotyping of dinucleotide-repeat microsatellites, and paternity testing. These examples are only illustrative embodiments of the present invention, and their description below is not intended to limit either its scope or its applications. In other words, the claim extends to other applications and procedures that embody the spirit of the present invention.

EXAMPLES

The following examples are provided only for the purpose of illustrating the invention and are not to be deemed as limiting the invention in any manner.

Example 1

Detection and/or Prevention of Errors in the Genotyping of Dinucleotide Repeat Microsatelites The following example illustrates in detail how to use the GEDAP method for detecting and/or preventing errors in dinucleotide repeat typing from human samples.

1. Samples, DNA Extraction and Markers 405 unrelated individuals living in Galicia (NW Spain) were analysed. DNA was extracted from whole blood samples using a commercial kit (QIAamp blood kit, QIAGEN). All individuals were genotyped for 6 dinucleotide repeats located on human chromosome 11: D11S4177, D11S1323, D11S4124, D11S1318, D11S909 and D11S1760 (Dib et al., 1996). ps 2. AMPLIFICATION The alleles of each marker present in each sample were amplified by the Polymerase Chain Reaction (PCR). The specific primer sequences for amplifying each locus were taken from the Généthon database. Amplifications were performed in a final volume of 25 µl, containing 120 ng genomic DNA, 10mM Tris-HCl (pH 9.0), 10% glycerol (v/v), 50 mM KCl, 0.1% Triton X-100, 1.5 mM MgCl2, 50 pmol of each primer, 200 µM dNTP mix, and 1 U Taq DNA polymerase. Amplifications were carried out in GeneAmp PCR System 2400 thermocyclers (Perkin-Elmer, Norwalk, CT, USA), and consisted of 35 cycles of denaturation (94° C., 40 s) and annealing (55° C., 30 s). After the last cycle, an additional extension step (72° C., 2 mm) completed the process.

3. Generation of Homoduplexes and DAPs

Thermal conditions used during amplification favoured the generation of homoduplexes and DAPs. In addition, the electrophoretic system used for detecting homoduplexes and DAP maintained at least some of the homoduplexes and DAP already formed and induced the formation of new DAPs (see section 5).

4. Detection of Homoduplexes and DAPs

The homoduplexes and DAPs generated from the amplification products of each sample were resolved by non-denaturing ultrathin-layer polyacrylamide gel electrophoresis using a discontinuous borate/formate buffer system.

Polyacrylamide gel thickness was 0.4 mm. Gel dimensions were 13.5 cm width by 20 cm length for loci D11S1760 and D11S909, and 13.5 cm width by 24 cm length for the remaining microsatellites analysed. The holder used for gel polymerization was a 2-mm-thick plain-glass plate treated with Bind Silane (Pharmacia 17-1330-01). Polyacrylamide pore size was 7.7% T 6.3% C for loci D11S1760 and D11S909, and 6.7% T 7.1% C for the remaining microsatellites analysed. The total monomer concentration (% T) and the total concentration of the crosslinker monomer (% C) were defined as % $T=[(a+b)/VT]100\%$ $T=[a/(a+b)]$ 100; a and b denote grams of acrylamide and piperazine diacrylamide (PDA), respectively, and TV the total volume of gel solution. The gel buffer was 0.33 M Tris, 110 mM formate, 24 mM borate, and 6% glycerol (v/v) (pH 9.0). 2.5 mM ammonium persulfate and 1.6 µl of TEMED (Merck 1.10732) per mililitre of gel solution were added for polymerization. Next, gels were keept in darkness at 37° C. during 20 minutes, prior to electrophoresis.

The electrode buffer was applied to the gel by two blotting pads of 1 cm in width (Blotting Paper, Sigma P-7176) dipped in 1 M Tris containing 0.28 M borate (pH 9.0). Pads were positioned at both ends of the gel and electrodes over the pads. The effective interelectrode distance in gels of 24 and 20 cm in length was 22 and 18 cm, respectively. Application tabs of fiberglass (IEF sample appl. piece, Pharmacia Biotech 80-1129-46), 3.3×2.5 mm, were used for sample application, at 0.5 cm from the cathode. Each tab contained 3 µl of each solution. The voltage and the running time used for each marker varied from 600 V to 700 V and from 2 h 30 min to 4 h, respectively (see the attached table). Intensity and power were kept constant at 25 mA and 20 W, respectively. Electrophoresis was performed at a constant temperature of 15° C. in the Multiphor II system (LKB Pharmacia), using Bromophenol Blue as migration marker.

Electrophoretic conditions used to resolve each microsatellite.

| Locus | D11S4177 | D11S1323 | D11S4124 | D11S1318 | D11S909 | D11S1760 |
|---|---|---|---|---|---|---|
| Voltage | 700 V | 700 V | 700 V | 600 V | 600 V | 600 V |
| Time | 4 h | 3 h 40 min | 3 h 15 min | 3 h 15 min | 2 h 45 min | 2 h 30 min |

After each electrophoresis had finished, homoduplexes and DAP were visualized by silver staining as described by Budowle et al. (1991).

Features of the electrophoretic system:

The electrophoretic system used for detecting the homoduplexes and the DAPs has several key features for reducing the chance of genotyping errors. On the one hand it ensures maintenance of homoduplexes and DAPs generated during the PCR, and at the same time induces the formation of new DAPs, so that it is useful for detecting and/or preventing genotyping errors by the GEDAP method. On the other hand, the system also allows resolution of amplification products from dinucleotide-repeat microsatellites with single base resolution and high precision in allele sizing. It is thus useful for reducing the likelihood of genotyping errors due both to the absence of single-base resolution (Smith et al., 1995; Schlötterer, 1998; Wenz et al., 1998), and to anomalous electrophoretic migrations among the alleles within a locus (Kimpton et al., 1995; Prinz et al., 1996).

Figure 6:
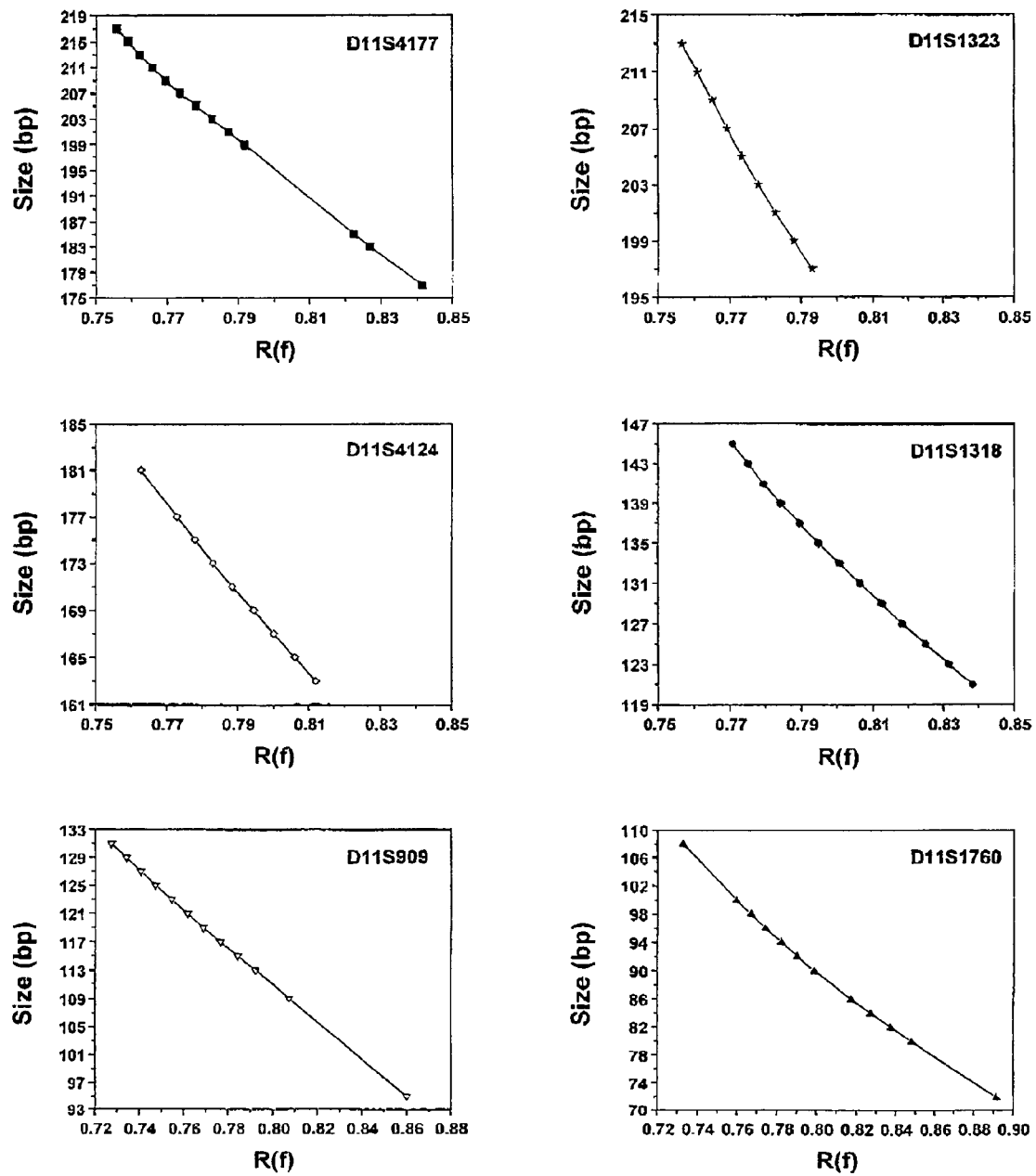
FIG. 6 shows electrophoretic-system resolution and precision, on the basis of R(f) values for the alleles of six dinucleotide-repeat microsatellites.

The resolution and precision of the electrophoretic system become apparent when the homoduplex band sizes are plotted against their relative mobilities, R(f), calculated as the migration distance from the anodal edge of the sample tab to the homoduplex band, divided by the distance from the anodal edge of the tab to the boundary. FIG. 6 shows the resolution and the precision of the electrophoretic system, under the conditions used for resolution of the alleles of the six microsatellites analysed. The observed R(f) differences among homoduplex bands that vary in size by two base pairs, are large enough to discriminate differences of a single base pair. Indeed, single-base differences among homoduplex bands from the dinucleotide-repeat microsatellite locus D11S1759, analysed in our laboratory, are clearly detectable using this electrophoretic system (data not shown).

FIG. 6 also shows that this electrophoretic system offers a high level of precision for sizing the homoduplex bands of dinucleotide-repeat microsatellites. It should be remembered that electrophoretic anomalies leading to inaccuracies in allele sizing are typically mobility shifts, band compression or among-allele differences in relative mobilities (Prinz et al., 1996). In FIG. 6, however, it can be seen that there is no evidence of this type of anomaly among the homoduplex bands of the loci analysed.

Figure 7:
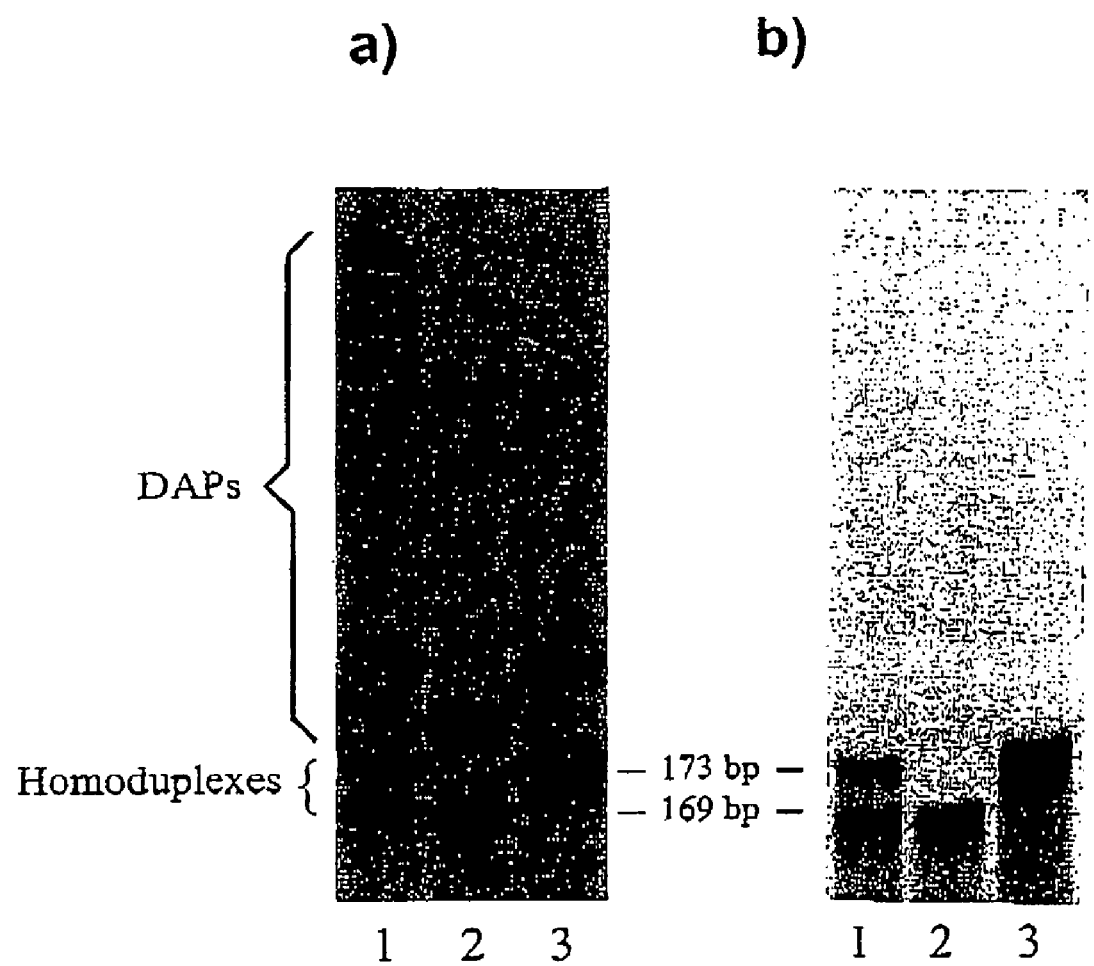
FIG. 7 shows two gels which illustrate how non-denaturing electrophoretic conditions favour the presence of DAPs, compared with denaturing electrophoretic conditions.

In addition, the characteristics of this electrophoretic system (non-denaturing conditions, high ionic strength, suitable temperature, etc.) allow maintenance of existing and induction of new homoduplexes and DAPs (FIG. 7, *a*). It is important to stress that the electrophoretic conditions decisively affect the detection of DAPs. FIG. 7, *b* shows how the use of both denaturing conditions and a running temperature of 50° C. lead to the detection of allele bands only. This is readily understood in view of the fact that DAPs result from the formation of complexes and/or from conformational changes of amplification products, and that the use of both denaturing conditions and a high temperature prevents the hybridization of nucleic acid strands. It must be remembered that this is the approach followed by conventional genotyping methods, and that the present invention is based on the contrary approach: that is, on the deliberate induction of DAP-generating complex formation and DAP-generating conformational changes.

5. Identification of Homoduplexes, DAP-ALs, DAP-HOMs, and DAP-HETs

Figure 8:
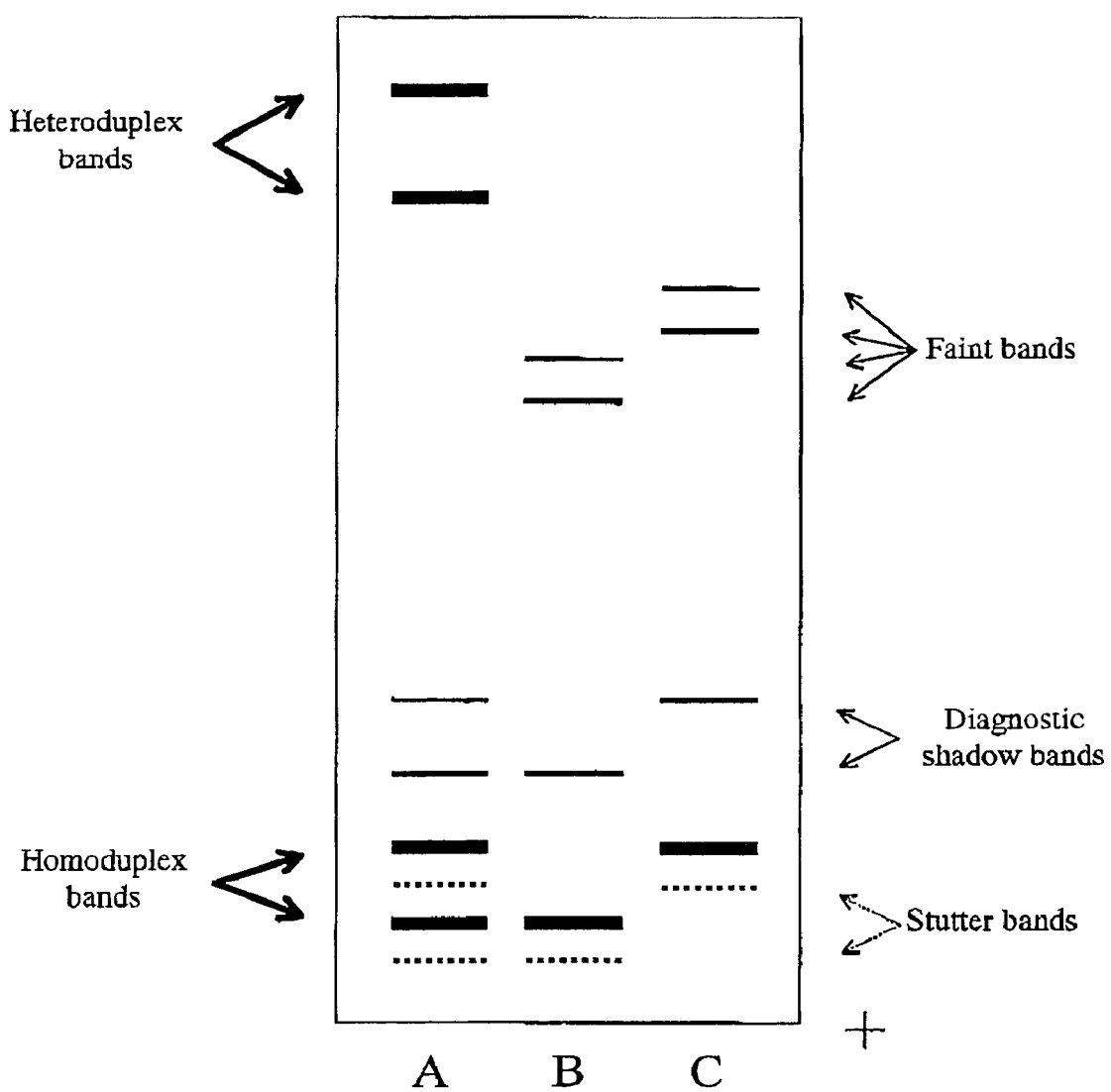
FIG. 8 provides a schematic illustration of bands corresponding to homoduplexes (homoduplex bands), to DAP-ALs (diagnostic shadow bands and stutter bands), to DAP-HOMs (faint bands) and to DAP-HETs (heteroduplex bands).

Homoduplexes and DAPs were identified from the band patterns observed in gels (FIG. 8).

5.1. Identification of Homoduplexes and DAP-ALs

On the one hand, this electrophoretic system allows the identification of homoduplexes and DAP-ALs from the observation of three types of bands: homoduplex bands, Diagnostic Shadow Bands (DSBs) and stutter bands (FIG. 8). All these types of band are useful for determining which allele or alleles have been amplified from each of the samples analysed.

Each homoduplex band arises from one of the homoduplexes generated from the amplified alleles, each homoduplex giving rise to a single homoduplex band. Homoduplex bands may be differentiated from the remaining bands because they generally have one associated DSB and at least one associated stutter band.

Stutter bands arise from DAP-ALs generated due to mistakes in allele amplification (particularly due to Taq polymerase slippage). In this electrophoretic system these bands were generally observed as single bands with a migration rate two bp higher than that of the corresponding homoduplex band. When stutter bands were revealed by silver staining, they showed lower intensity than the corresponding homoduplex band.

Each DSB arises from one DAP-AL resulting in turn from a conformational change in one homoduplex. DSBs are easily distinguishable from the remaining bands because they have a lower migration rate than the corresponding homoduplex band. In addition, [homoduplex band]-DSB distance is almost constant within each locus. It should also be noted that [homoduplex band]-DSB distance varies among loci (about 4 base pairs in D11S1760; 6 bp in D11S909; 8 bp in D11S4177, D11S4124, and D11S1318; and 14 bp in D11S1323).

5.2. Identification of DAP-HOMs and DAP-HETs

This electrophoretic system also allowed the identification of DAP-HOMs and DAP-HETs, from the observation of two types of bands: faint bands and heteroduplex bands (FIG. 8). Both types of band are useful for determining whether the analysed sample is homozygous or heterozygous for a dinucleotide-repeat microsatellite.

Heteroduplex bands arise from DAP-HETs. Heteroduplex bands are easily distinguishable from the remaining bands because [homoduplex band]-[heteroduplex band] distance is higher than [homoduplex band]-[DSB distance].

Faint bands arise from DAP-HOMs. Faint bands are easily distinguishable from the remainder bands because [homoduplex band]-[faint band distance] is higher than [homoduplex band]-[DSB distance]. In addition, [homoduplex band]-[faint band] distance is generally lower than [homoduplex band]-[heteroduplex band] distance.

6. Detection and/or Prevention of Genotyping Errors

The GEDAP method allowed us to detect and/or prevent a relatively large number of genotyping errors due to total or partial non-amplifications. To this end, two strategies were adopted: one for detecting errors and one for preventing errors. Both strategies are based on the joint analysis of the bands described in the previous section. In what follows, we show how the two strategies were applied for genotyping the six dinucleotide-repeat microsatellites. The efficacy of the method will be evaluated subsequently (see Section 7).

6.1—Detection of Genotyping Errors

Figure 9:
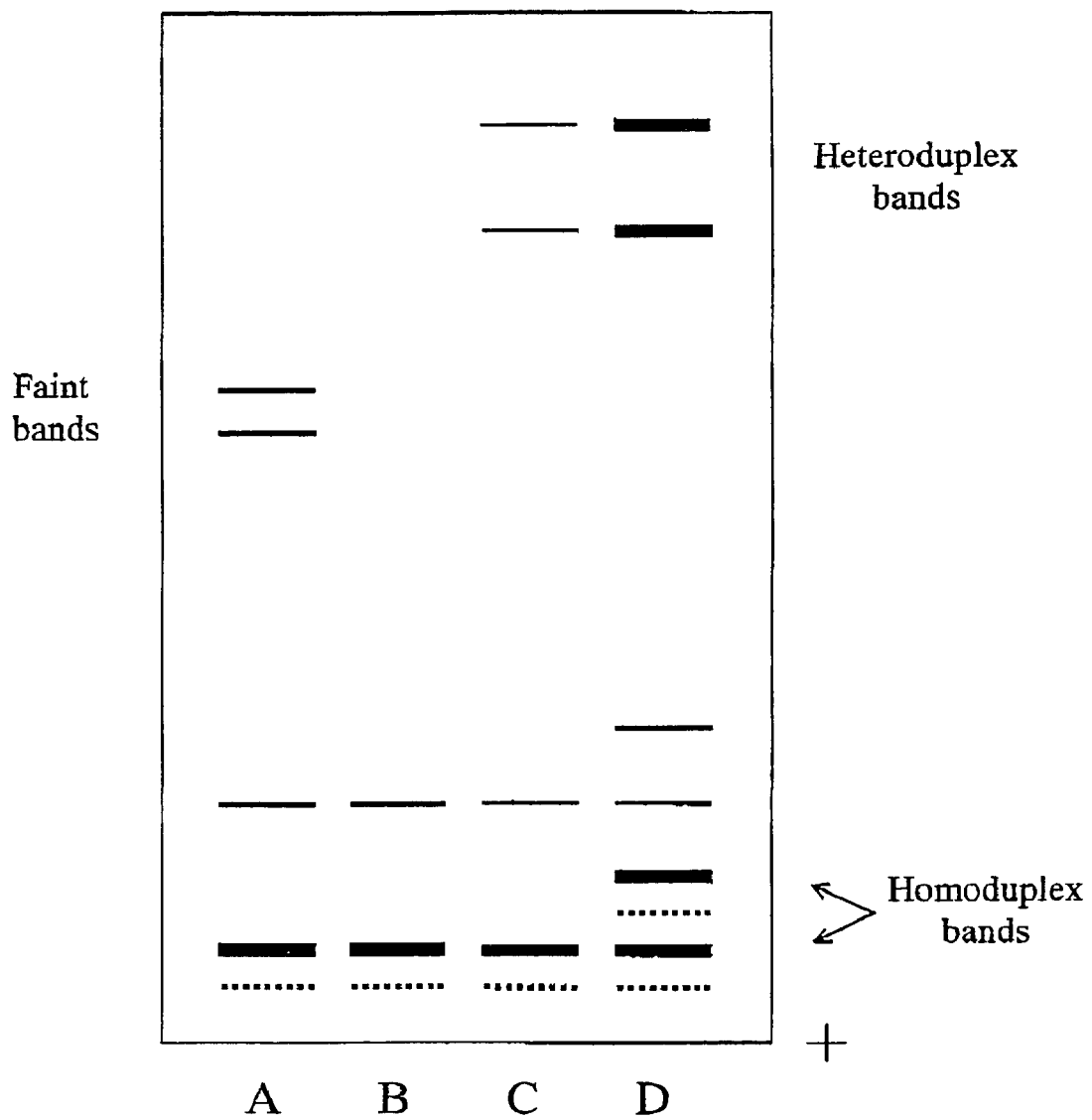
FIG. 9 provides a schematic illustration of the detection of genotyping errors by the GEDAP method, through the identification of anomalous band patterns (B and C), compared with normal band patterns (A and D).

The GEDAP method allowed us to detect genotyping errors due to total or partial non-amplifications. Genotyping errors were detected from samples with anomalous band patterns, as follows:

(a) Patterns with a single homoduplex band and without any faint band (FIG. 9,
  B); compare with the specific band pattern expected for a homozygous genotype (FIG. 9, A).
(b) Patterns with a single homoduplex band and at least one heteroduplex band (FIG. 9, C); compare with the specific band pattern expected for a heterozygous genotype (FIG. 9, D).

In order to detect genotyping errors, we analysed the band patterns of 405 unrelated individuals (a sample size large enough for detecting the possible occurrence of genotyping errors) and performed replicate analyses of all apparently homozygous samples without faint bands or with at least one heteroduplex band in their corresponding band patterns. The repeat analyses were performed until faint bands, or the presence of a band pattern corresponding to a heterozygote, were observed.

The results obtained confirmed that a high proportion of apparently homozygous samples without faint bands were in fact heterozygous samples in which there has been total non-amplification of one of the two alleles. The GEDAP method is thus useful for detecting genotyping errors due to total non-amplifications. The frequency of the genotyping errors detected by this approach ranged from 0% (loci D11S1323 and D11S1760) to 2% (locus D11S909) of individuals. Different individuals showed genotyping errors at different loci: individuals 37, 39, 57, 62, 263, 351 and 398 at D11S4177; individuals 104, 311 and 400 at D11S4124; individual 134 at D11S1318; and individuals 48, 80, 216, 281 and 289 at D11S909. When all six $(AC)_n$ repeats are considered, the error rate was 5% (19/405). It is important to note that the rate of misidentification of multilocus genotypes might be substantially increased in studies in which a large number of loci are analysed, as in the case of genome scans.

In addition, the results obtained of the repeat analyses also confirmed that the apparently homozygous samples showing at least one heteroduplex band in their band patterns were in fact heterozygous samples in which there has been a total or partial non-amplification of one of the two alleles. The GEDAP method is thus also useful for detecting genotyping errors due to partial non-amplifications.

6.2—Prevention of Genotyping Errors

The GEDAP method also allows prevention of genotyping errors. To this end, two approaches were adopted: one for preventing errors in the genotyping of heterozygous samples, the other for preventing errors in the genotyping of homozygous samples.

6.2.1. Prevention of Errors in the Genotyping of Heterozygous Samples

The approach used for preventing errors in the genotyping of heterozygous samples consisted of genotyping a sample as heterozygous only when the electrophoretic system generated a band pattern including two homoduplex bands and:

(a) at least one heteroduplex band; and/or
(b) at least one DSB associated with each of the homoduplex bands and/or
(c) at least one stutter band associated with each of the homoduplex bands.

The reproduction of heterozygous band patterns by mixing homozygous DNAs prior to PCR, and the population analysis of 405 unrelated individuals, confirmed that this criterion set is sufficient for correct identification of heterozygous samples. In addition, the use of this approach allowed us to prevent a considerable number of genotyping errors due to partial non-amplifications. The experimental data supporting these assertions are now described.

Figure 10:
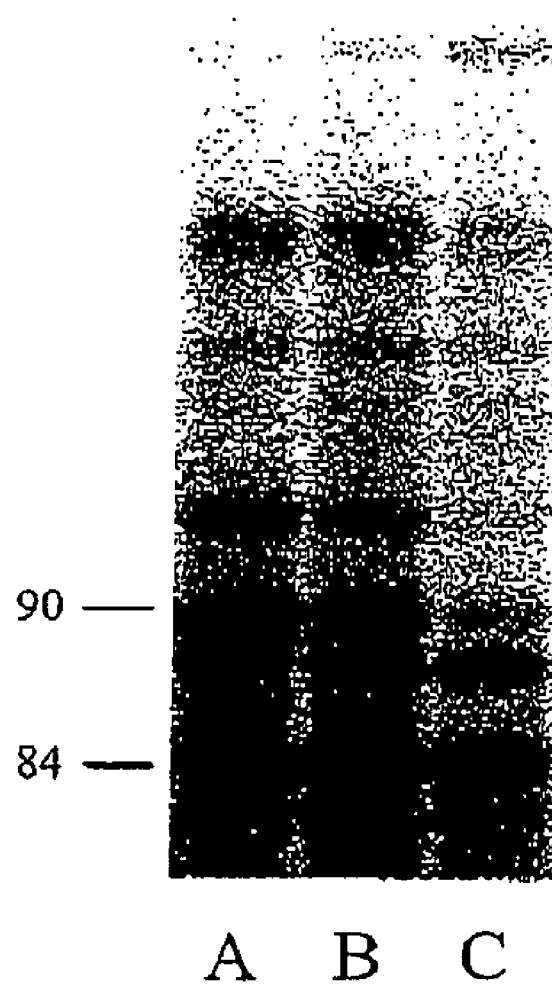
FIG. 10 shows a gel which illustrates the prevention of errors in the genotyping of heterozygous samples by the GEDAP method, through the joint analysis of homoduplex bands, diagnostic shadow bands, stutter bands, faint bands and heteroduplex bands.

FIG. 10 show how errors in the genotyping of heterozygous samples due to total and partial non-amplifications may be prevented on the basis of the joint analysis of the bands generated by the electrophoretic system. The figure shows the specific band pattern for a heterozygous genotype (alleles 90 and 84 in D11S1760) in the absence (FIG. 10, B) and in the presence (FIG. 10, A and C) of partial non-amplification. The band pattern of this genotype was reproduced by conditions inducing partial non-amplification (FIG. 10, A and C): specifically, the DNAs from two homozygous individuals were mixed in unequal proportions and amplification was performed from the mixed DNAs.

The results obtained after inducing partial non-amplification of one of the two alleles of the heterozygous genotype revealed a marked difference in the intensity of the homoduplex bands generated from the two alleles (FIG. 10, A and C). If only band intensities are taken into account (as in conventional genotyping methods), then the intensity difference between the two bands may lead to a genotyping error. The GEDAP method, however, prevents such errors. This is due to the fact that both the specific heteroduplex bands of genotype 90/84 and the stutter bands associated with the homoduplex bands generated from alleles 90 and 84 are present in band patterns obtained after inducing the partial non-amplification of each of the alleles of this genotype. These bands are thus useful for preventing errors in the genotyping of heterozygous samples due to partial non-amplifications.

The use of this approach in the analysis of 405 unrelated individuals prevented genotyping errors due to the partial non-amplification of one allele in a relatively large number of heterozygous samples. For example, in D11S4177 heterozygotes with the 183-bp allele and a larger allele, the 183-bp allele showed partial non-amplification more frequently than the other alleles. Similarly, this approach allowed us to prevent genotyping errors due to partial non-amplifications in heterozygotes for alleles with small differences in size, at all six loci analysed. The GEDAP method is therefore useful for preventing genotyping errors due to partial non-amplifications.

Nevertheless, it is important to note that the approach used in the GEDAP method for genotyping heterozygous samples may not be used for genotyping homozygous samples. That is, the absence of heteroduplex bands and/or the two stutter bands and/or the two DSBs corresponding to the two homoduplex bands is not sufficient to identify a sample genotype as homozygous. Indeed, genotyping dinucleotide-repeat microsatellites taking into account only the homozygous-sample genotyping strategy may increase the rate of genotyping errors, as we have previously demonstrated, because the amplification products of heterozygous samples lack heteroduplex bands when total non-amplification occurs. An alternative strategy for preventing errors in the genotyping of homozygous samples is thus needed.

6.2.2. Prevention of Errors in the Genotyping of Homozygous Samples

The approach used in the GEDAP method for preventing errors in the genotyping of homozygous samples consists of genotyping a sample as homozygous only when the electrophoretic system generates a band pattern in which one homoduplex band and at least one faint band are detected.

The results obtained from the analysis of 405 unrelated individuals showed that faint bands are always present in band patterns in which only one homoduplex band is detected, except for band patterns of heterozygous samples with total non-amplification of one of their alleles (see Section 6.1). Faint bands thus constitute an additional level of control for preventing genotyping errors that lead to misidentification of heterozygotes as homozygotes.

7. Efficacy of the GEDAP Method

Efficacy was evaluated statistically by testing whether the genotype frequencies observed in the sample of 405 unrelated individuals deviate significantly from the genotype proportions expected under Hardy-Weinberg (HWP).

Deviations from HWP for each locus and each allele, and their statistical significance, were estimated following the procedure described by Robertson and Hill (1984). The attached table shows that the observed and expected genotype frequencies are in good agreement at all loci, with no statistically significant deviations from HWP.

| Deviations from HWP for each locus ($f_T$) and their significance ($X^2$). | | | | |
| --- | --- | --- | --- | --- |
| Locus | Obs. Het. | Exp. Het.[a] | $f_T \pm$ S.E. | $X^2$ (g.l. = 1) |
| D11S4177 | 0.795 | 0.788 | 0.005 ± 0.020 | 0.12 |
| D11S1323 | 0.625 | 0.617 | 0.001 ± 0.018 | 0.01 |
| D11S4124 | 0.723 | 0.710 | 0.001 ± 0.018 | 0.00 |
| D11S1318 | 0.817 | 0.805 | −0.001 ± 0.011 | 0.01 |
| D11S909 | 0.723 | 0.738 | 0.024 ± 0.039 | 2.51 |
| D11S1760 | 0.807 | 0.782 | −0.015 ± 0.000 | 1.03 |

[a]Unbiased expected heterozygosities were calculated by the equation $$h = 2n\left(1 - \sum_{i=1}^{k} p_i^2\right) / 2n - 1$$

(Nei and Roychoudhury, 1974).

On the other hand, only one of the 68 alleles deviated significantly from HWP (data not shown). However, this significant deviation can be attributed to type I error, so that the observed genotype frequencies for each allele can in fact be considered consistent with HWP. In addition, the departures from HWP detected by the $f$-statistic were small and non-systematic. Taken together, we did not find any evidence for a significant presence of non-amplifications that lead to misidentification of heterozygotes as homozygotes. The results obtained by this analysis thus confirm that the GEDAP method is effective for detecting and/or preventing genotyping errors due to total or partial non-amplifications.

Example 2

Paternity Testing

The following example illustrates the usefulness of the GEDAP method for identifying human individuals accurately. In particular, we show how the method prevents false exclusion of parentage.

This application is here demonstrated by the genotyping, in biologically related Caucasian individuals, of all the six dinucleotide-repeat microsatelites used in example 1.

DNA extraction, amplification of markers, and generation, detection and identification of homoduplexes and DAP were carried out according to sections 1, 2, 3, 4 and 5 from Example 1.

Figure 11:
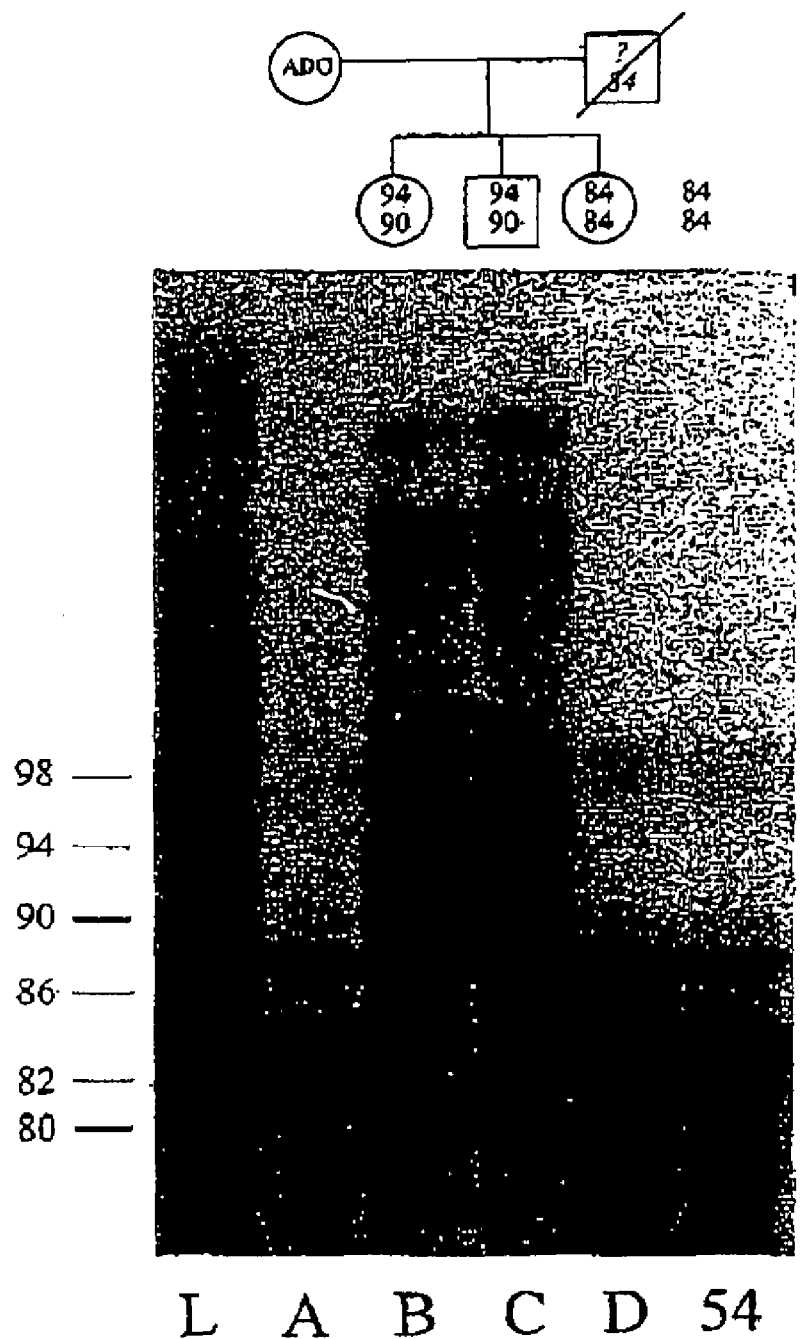
FIG. 11 shows a gel which suggests an apparent parentage exclusion detected by the D11S1760 dinucleotide repeat.

FIG. 11 shows one non-Mendelian result for D11S1760. On the basis of conventional genotyping methods (i.e., taking into account only the homoduplex bands generated from the alleles for each individual), one could conclude that two offspring of individual A (individuals B and C), are in fact not children of that individual. In particular, individual A only shows one homoduplex band (generated from allele 84) and the corresponding associated bands: one DSB and one stutter band. Conventional genotyping methods would therefore identify this individual as homozygous 84/84. If this were the real genotype of individual A, she should necessarily pass one allele 84 to each of her children. Individuals B and C, however, did not show in their band patterns any homoduplex band generated from allele 84. On the contrary, both showed the band pattern typical of genotype 94/90: that is, two homoduplex bands (generated from alleles 94 and 90, respectively), the corresponding DSBs and stutter bands associated with the two homoduplex bands, and three heteroduplex bands typical of genotype 94/90.

Figure 12:
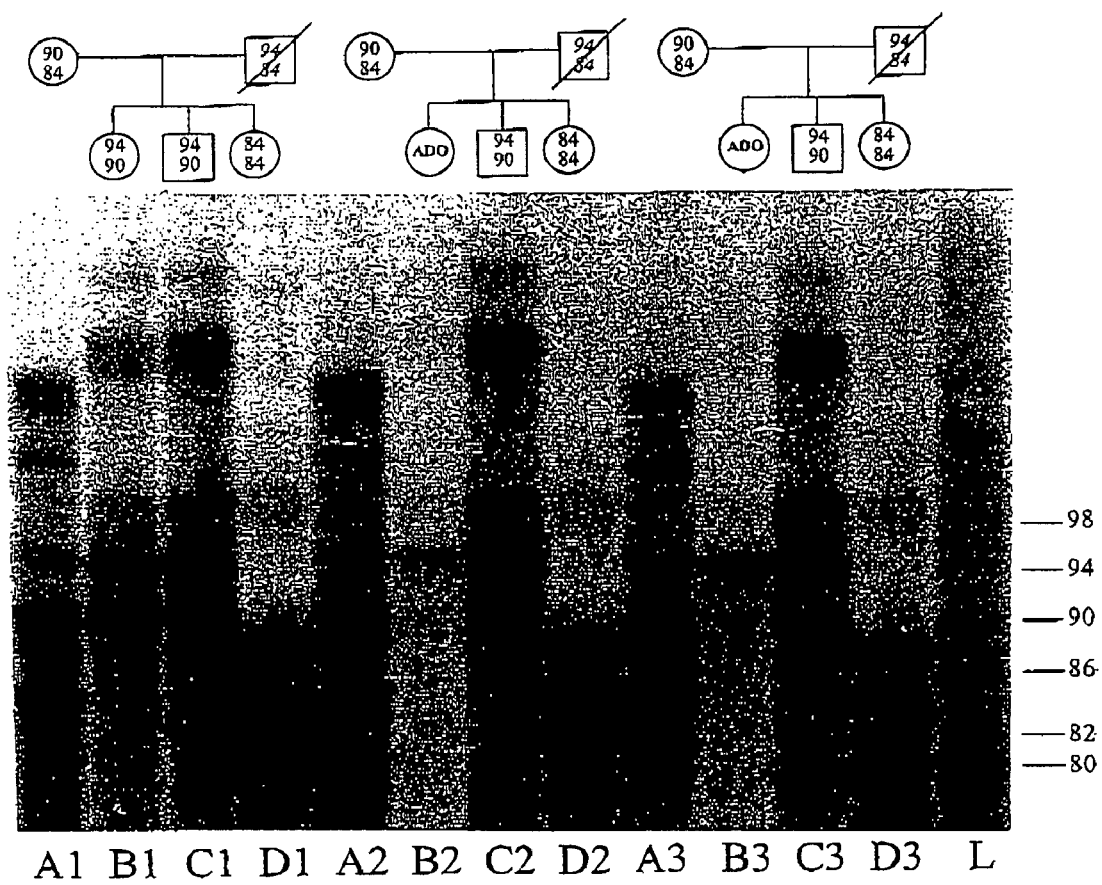
FIG. 12 shows a gel which illustrates how the GEDAP method reveals that the apparent parentage exclusion of FIG. 11 is in fact a genotyping error due to a total non-amplification.

The GEDAP method, however, detected this false parentage-exclusion and demonstrated that the apparent non-Mendelian result was actually due to total non-amplification of one allele in individual A. In particular, the analysis of the band pattern of individual A by the GEDAP method makes evident that this is an anomalous band pattern in which only one homoduplex band and no faint bands are detected (FIG. 11, A: compare with the band patterns of samples D and 54, which presented the faint bands specific for genotype 84/84). As was demonstrated in Example 1, the presence of this anomalous band pattern is strongly indicative of total non-amplification. To investigate this possibility, we performed three repeat PCR analyses of each of the members of this family (FIG. 12). The three replicates confirmed that the apparent parentage problem initially detected was in fact an error in the genotyping of individual A, due to the total non-amplification of allele 90. The analysis of the remaining five markers confirmed this observation.

The GEDAP method is therefore effective for detecting and preventing false parentage-exclusions. Indeed, the GEDAP method also allowed us to rule out a new apparent parentage-exclusion suggested by two of the individual-B replicates (B2 and B3, FIG. 12). In both replicates, the band patterns generated for this individual only showed the homoduplex corresponding to allele 94 (absent in the mother). However, both patterns were again anomalous (because faint bands were undetected), so that, as in the previous instance, the GEDAP method revealed that these apparent parentage-exclusions are in fact the result of the total non-amplification of allele 90.

REFERENCES

Akey, J. M., Zhang, K., Xiong, M., Doris, P. et al. (2001) *Am. J. Hum. Genet.* 68: 1447-1456.

Anderson, T. J. C., Paul, R. E. L., Donelly, C. A., Day, K. P. (2000) *Genet. Res.* 75: 285-296.

Applied Biosystems. (2001) *Biosystems Solutions* 1: 10.

Ardren, W. R., Borer, S., Thrower, F., Joyce, J. E. et al. (1999) *J. Hered.* 90: 529-536.

Beacauge et al. (1981) *Tethrahedron Letters* 22: 1859-1862.

Belotserkovskii, B. P., Johnston, B. H. (1996) *Electrophoresis* 17: 1528-1534.
Budowle, B., Chakraborty, R., Giusti, A. M., Eisenberg, A. J. et al. (1991) *Am. J. Hum. Genet.* 48: 137-144.
Buetow, K. H. (1991) *Am. J. Hum. Genet.* 49: 985-994.
Caruthers, M. H., Barone, A. D., Beacauge, S. L., Dodds, D. R. et al. (1988) *Methods Enzymol.* 154: 287-314.
Casasnovas, J. M., Huertas, D., Ortiz-Lombardía, M., Kypr, J. et al. (1993) *J. Mol. Biol.* 233: 671-681.
Chakraborty, R., de Andrade, M., Daiger, S. P., Budowle, B. (1992) *Ann. Hum. Genet.* 56: 45-57.
de La Chapelle, A., Wright, F. A. (1998) *Proc. Natl. Acad. Sci. USA* 95: 12416-12423.
Deka, R., de Croo, S., Yu, L. M., Ferrell, R. E. (1992) *Hum. Genet.* 90: 86-90.
Demers, D. B., Curry, E. T., Egholm, M., Sozer, A. C. (1995) *Nucleic Acids Res.* 23: 3050-3055.
Dib, C., Fauré, S., Fizames, C., Samson, D. et al. (1996) *Nature* 380: 152-154.
Dolinnaya, N. G., Braswell, E. H., Fossella, J. A., Klump, H. et al. (1993) *Biochemistry* 32: 10263-10270.
Dolinnaya, N. G., Fresco, J. R. (1992) *Proc. Natl. Acad. Sci. USA* 89: 9242-9246.
Douglas, J. A., Boehnke, M., Lange, K. (2000) *Am. J. Hum. Genet.* 66: 1287-1297.
Dr bek, J, (2001) *Electrophopesis* 22: 1024-1045.
Durland, R. H., Kessler, D. J., Gunell, S., Duvic, M. et al. (1991) *Biochemistry* 30: 9246-9255.
Ewen, K. R., Bahlo, M., Treloar, S. A., Levinson, D. F. et al. (2000) *Am. J. Hum. Genet.* 67: 727-736.
Findlay, I., Ray, P., Quirke, P., Rutherford, A. et al. (1995) *Hum. Reprod.* 10: 1609-1618.
Fishback, A. G., Danzmann, R. G., Sakamoto, T., Ferguson, M. M. (1999) *Aquaculture* 172: 247-254.
Frank-Kamenetskii, M. D., Mirkin, S. M. (1995) *Annu. Rev. Biochem.* 64: 65-95.
Gagneux, P., Boesch, C., Woodruff, D. (1997) *Mol. Ecol.* 6: 861-868.
Gaillard, C., Strauss, F. (1994) *Science* 264: 433-436.
Garvin, A. M., Holzgreve, W., Hahn, S. (1998) *Nucleic Acids Res.* 26: 3468-3472.
Goldstein, D. R., Zhao, H., Speed, T. P. (1997). *Hum Hered.* 47: 86-100.
Gomes, I., Collins, A., Lonjou, C., Thomas, N. S. et al. (1999) *Ann. Hum. Genet.* 63: 535-538.
Göring, H. H. H., Terwilliger J. D., Ott, J. (1997) *Am. J. Hum. Genet.* 61: 1614.
Göring, H. H. H., Terwilliger, J. D. (2000) *Am. J. Hum. Genet.* 66: 1107-1118.
Haddad, L. A., Fuzikawa, A. K., Pena, S. D. J. (1997) *Hum. Genet.* 99: 796-800.
Handyside, A. H., Delhanty, J. D. A. (1997) *Trends Genet.* 13: 270-275.
Haralambidis, J., Duncan, L., Angus, K., Treagear, G. W. (1990) *Nucleic Acids Res.* 18: 1055-1067.
Harper, J. C., Coonen, E., Handyside, A. H. et al. (1995) *Prenat. Diagn.* 15: 41-49.
Huertas, D., Bellsolell, L., Casasnovas, J. M., Coll, M. et al. (1993) *EMBO J.* 12: 4029-4038.
Kimpton, C. P., Gill, P., d'Aloja, E., Andersen, J. F. et al. (1995) *Forensic Sci. Int.* 71: 137-152.
Lareu, V., Pestoni, C., Phillips, C., Barros, F. et al. (1998) *Electrophoresis* 19: 1566-1572.
Lee, J. S. (1990) *Nucleic Acids Res.* 18: 6057-6060.
Lissens, W., Sermon, K. (1997) *Hum. Reprod.* 12: 1756-1761.
Miller, M. J., Yuan, B. Z. (1997) *Anal. Biochem.* 251: 50-56.
Mukerji, I., Shiber, M. C., Fresco, J. R., Spiro, T. G. (1996) *Nucleic Acids Res.* 24: 5013-5020.
Mullis, K., Faloona, F., Scharf, S., Saiki, R. et al. (1986) Cold Spring Harb. Symp. Quant. Biol. 51 Pt 1: 263-273.
Mutter, G. L., Boynton, K. A. (1995) *Nucleic Acids Res.* 23: 1411-1418.
Nei, M., Rychoudhury, A. K. (1974) *Genetics* 76: 379-390.
Neilan, B. A., Leigh, D. A., Rapley, E., McDonald, B. L. (1994) *BioTechniques* 17: 708, 710, 712.
Noonberg, S. B., Franç ois, J. C., Garestier, T., Hélène, C. (1995) *Nucleic Acids Res.* 23: 1956-1963.
Ortiz-Lombardía, M., Eritja, R., Azorín, F., Kypr, J. et al. (1995) *Biochemistry* 34: 14408-14415.
Pemberton, J. M., Slate, J., Bancroft, D. R., Barrett, J. A. (1995) *Mol. Ecol.* 4: 249-252.
Perlin, M. W., Burks, M. B., Hoop, R. C. Hoffman, E. P. (1994) *Am. J. Hum. Genet.* 55: 777-787.
Prinz, M., Schmitt, C., Staak, M., Baum, H. (1996) *Electrophoresis* 17: 1190-1193.
Ray, P. F., Handyside, A. H. (1996) *Mol. Hum. Reprod.* 2: 213-218.
Robertson, A., Hill, W. G. (1984) *Genetics* 107: 703-718.
Ronai, Z., Guttman, A., Nemoda, Z., Staub, M. et al. (2000) *Electrophoresis* 21: 2058-2061.
Saiki, R. K., Scharf, S., Faloona, F., Mullis, K. B. et al. (1985) *Science* 230: 1350-1354.
Schlotterer, C. (1998) Microsatellites, pp. 237-261. In: A. R. Hoelzel (Ed.), Oxford University Press.
Shiber, M. C., Braswell, E. H., Klump, H., Fresco, J. R. (1996) *Nucleic Acids Res.* 24: 5004-5012.
Smith, J. R., Carpten, J. D., Brownstein, M. J., Ghosh, S. et al. (1995) *Genome Res.* 5: 312-317.
Szibor, R., Plate, I., Krause, D. (1996) *Adv. Forensic Haemogenet.* 6: 346-348.
Taberlet, P. (1997) *Nucleic Acids Res.* 25: 967.
Taberlet, P., Griffin, S., Goossens, B., Questiau, S. et al. (1996) *Nucleic Acids Res.* 24: 3189-3194.
Terwilliger, J. D., Shannon, W. D., Lathrop, G. M., Nolan, J. P. et al. (1997) *Am. J. Hum. Genet.* 61: 430-438.
Tóth, G., Gáspári, Z., Jurka, J. (2000) Genome Res. 10: 967-981.
Vorlícková, M., Kejnovská, I., Kovanda, J., Kypr, J. (1998) *Nucleic Acids Res.* 26: 1509-1514.
Walsh, P. S., Erlich, H. A., Higuchi, R. (1992) *PCR Methods Appl.* 1: 241-250.
Weeks, D. E., Conley, Y. P., Mah, T. S., Otis Paul, T. et al. (2000) *Hum. Mol. Genet.* 9: 1329-1349.
Weissensteiner, T. (1997) *Nucleic Acids Res.* 25: 966.
Weissensteiner, T., Lanchbury, J. S. (1996) *BioTechniques* 21: 1102-1108.
Wenz, H., Robertson, J. M., Menchen, S., Oaks, F. et al. (1998) *Genome Res.* 8: 69-80.
Wilkin, D. J., Koprivnikar, K. E., Cohn, D. H. (1993) *Genomics* 15: 372-375.
Yue, P. K., Kricka, L. J., Fortina, P., Panaro, N. J. et al. (2001) *Genome Res.* 11: 405-412.
Zapata, C., Rodríguez, S., Visedo, G., Sacristán, F. (2001a) *Genetics* 158: 1235-1251.
Zapata, C., Carollo, C., Rodríguez, S. (2001b) *Ann. Hum. Genet.* 65: 395-406.

The invention claimed is:

1. A method for at least one of detecting and preventing genotyping errors due to total or partial non-amplifications of a polymorphic locus, the method comprising the following steps:

a) obtaining a nucleic acid originating from at least one eukaryotic cell;

b) amplifying a nucleic acid sequence by PCR which allows the denaturation of double-stranded nucleic acids and their subsequent renaturation for inducing generation of homoduplexes of amplified alleles and other diagnostic additional products (DAPs) that are specific for at least one of homozygotes (DAPs-HOM), heterozygotes (DAPs-HET) and alleles (DAPs-AL), wherein said DAPs are additional amplification products specific to at least one genotype or allele resulting from at least one of an alteration of the sequence of the DNA template, a formation of intermolecular complexes and conformational changes of amplification products;

c) detecting the amplification products by an analytical procedure under non-denaturing conditions that favor at least one of the maintenance of homoduplexes and DAPs generated in PCR, and the maintenance of new DAPs generated once the PCR has finished by denaturing the amplification products by physical, chemical or biological procedures and subsequent renaturing; and d) performing the genotyping on the basis of the joint analysis of identified homoduplexes and DAPs wherein genotyping errors of genuinely heterozygous samples as homozygous samples due to total or partial non-amplifications are detected from the absence of DAPs specific to homozygotes (DAPs-HOM) and genotyping errors of genuinely heterozygous samples as homozygous samples due to total or partial non-amplifications are prevented from the presence of at least one of DAPs specific to alleles (DAPs-AL) and of heterozygotes (DAPs- HET).

2. The method, according to step (b) of claim 1, wherein the Additional Products include all those amplification products that are different than the homoduplexes generated from sample alleles.

3. The method, according to step (b) of claim 1, wherein the Additional Products are selected from the group consisting of:
   a) a single-stranded nucleic acid with a sequence different to those of the strands of alleles amplified from a sample;
   b) a double-stranded nucleic acid with a sequence different to those of the homoduplexes generated from sample alleles;
   c) a double-stranded nucleic acid constituted by strands that are not totally complementary;
   d) an amplification product which results from the interaction between at least one single strand generated during the amplification and at least one component of the reaction mixture used for the amplification;
   e) an amplification product which results from the interaction between at least one single strand generated during the amplification and at least one component of a system used for the detection of amplification products;
   f) an amplification product which results from the hybridization of three or more strands generated during the amplification;
   g) a conformational change of any of the homoduplexes;
   h) a conformational change of any of the Additional Products;
   i) an amplification product which results from the interaction between at least one homoduplex and at least one Additional Product;
   j) an amplification product which results from the interaction between at least two homoduplexes; and
   k) an amplification product which results from the interaction between at least two Additional Products.

4. The method according to claim 1, wherein at least one allele of a locus of interest is amplified by PCR.

5. The method according to step (c) of claim 1, wherein new DAPs are generated once the PCR has finished by denaturing procedures selected from the group consisting of thermal denaturation, electrochemical denaturation by voltage application, enzymes and denaturing agents.

6. The method according to claim 5, wherein denaturing agents are selected from the group consisting of fonnamide, urea and EDTA.

7. The method according to claim 5, wherein new DAPs are generated once the PCR has finished by at least one of changes of temperature, of salt-concentration, of pH and of bivalent ions concentration.

8. The method according to step (c) of claim 1, wherein the analytical procedure under non-denaturing conditions is selected from the group consisting of non-denaturing electrophoresis, mass spectrometry, chromatography, differential hybridization and sequencing by hybridization.

9. The method, according to step (d) of claim 1, wherein the genotyping is performed by the joint analysis of identified homoduplexes and DAPs by a manual or by a mechanical procedure.

10. The method, according to claim 1, wherein the mechanical procedure is a computer, is computer-based or is a computer-like apparatus.

11. The method according to claim 1, wherein genotyping errors due to partial or total non-amplifications of dinucleotide-repeat microsatellites are at least one of detected and prevented by separation of the amplification products with non-denaturing electrophoresis, and subsequent joint analysis of the bands of the homoduplexes, faint bands (DAPs-HOM), heteroduplex bands (DAPs-HET), and diagnostic shadow bands and stutter bands (DAPs-AL), presents and absents.

12. The method according to claim 11, wherein the separation of amplification products is performed with a horizontal ultrathin-layer electrophoretic system with polyacrylamide gels that contain glycerol, a concentration of the piperazine diacrylamide crosslinker higher that 5%, using non-denaturing conditions, a discontinuous borate/formate buffer system with high ionic strength, and a running temperature during the electrophoresis of less than 50° C.

13. The method according to claim 11, wherein the system permits resolution and accurate sizing of bands differing from each other by one base pair, over a size range of at least 70-220 base pairs.

14. The method, according to claim 11, wherein stutter bands are identified with the system and wherein:
   a) the stutter bands are associated with each of the homoduplex bands;
   b) the stutter bands have a higher migration rate than their corresponding homoduplex bands; and
   c) the intensity of stutter bands diminishes gradually when the stutter band homoduplex band distance increases.

15. The method according to claim 11, wherein diagnostic shadow bands are identified with the system and wherein:
   a) the diagnostic shadow bands are associated with each of the homoduplex bands;
   b) the diagnostic shadow bands have a lower migration rate than their corresponding homoduplex bands; and
   c) the diagnostic shadow bands have a higher migration rate than the faint bands or the heteroduplex bands generated from the amplification products of a sample.

16. The method according to claim 11, wherein faint bands are identified with the system and wherein:
  a) the faint bands have a lower migration rate than the corresponding homoduplex bands and diagnostic shadow bands; and
  b) the faint bands are generally detected only if there is one homoduplex band.

17. The method according to claim 11, wherein heteroduplex bands are identified with the system and wherein:
  a) the heteroduplex bands have a lower migration rate than the corresponding homoduplex bands and diagnostic shadow bands; and
  b) the heteroduplex bands are generally detected if there is more than one homoduplex band.

18. The method according to claim 1, wherein genotyping errors due to total or partial non-amplifications in diploid and polyploid samples are at least one of detected and prevented.

19. The method according to claim 1, wherein genotyping errors due to total or partial non-amplifications from the amplification products involving more than one locus andlor in high throughput genotyping are at least one of detected and prevented, and wherein said method includes the use of a partially or totally automated system.

20. The method according to claim 1, wherein genotyping errors due to total or partial non-amplifications are at least one of detected and prevented in a use selected from the group consisting of disease diagnosis, preimplantational genetic diagnosis, paternity testing, forensic analyses, genetic therapy, tissue and organ transplantation, pharmacogenetics, population genetics, genome mapping and genetic epidemiology.

* * * * *